United States Patent
Foody

(10) Patent No.: US 11,760,630 B2
(45) Date of Patent: Sep. 19, 2023

(54) PROCESS AND SYSTEM FOR PRODUCING LOW CARBON INTENSITY RENEWABLE HYDROGEN

(71) Applicant: Iogen Coproration, Ottawa (CA)

(72) Inventor: Patrick J. Foody, Ottawa (CA)

(73) Assignee: Iogen Corporation, Ontario (CA)

( * ) Notice: Subject to any disclaimer, the term of this patent is extended or adjusted under 35 U.S.C. 154(b) by 0 days.

(21) Appl. No.: 18/069,041

(22) Filed: Dec. 20, 2022

(65) Prior Publication Data

US 2023/0183064 A1 Jun. 15, 2023

Related U.S. Application Data

(63) Continuation of application No. PCT/CA2022/050586, filed on Apr. 14, 2022.

(60) Provisional application No. 63/201,168, filed on Apr. 15, 2021.

(51) Int. Cl.
| | | |
|---|---|---|
| *C01B 3/34* | (2006.01) | |
| *C01B 3/50* | (2006.01) | |
| *C10K 1/00* | (2006.01) | |
| *C10L 3/10* | (2006.01) | |
| *B01D 53/047* | (2006.01) | |

(52) U.S. Cl.
CPC .............. *C01B 3/50* (2013.01); *B01D 53/047* (2013.01); *C01B 3/34* (2013.01); *C10K 1/005* (2013.01); *C10L 3/104* (2013.01); *B01D 2257/504* (2013.01); *C01B 2203/0216* (2013.01); *C01B 2203/1241* (2013.01); *C01B 2203/86* (2013.01); *C10L 2200/0469* (2013.01); *C10L 2290/26* (2013.01)

(58) Field of Classification Search
CPC ..... C01B 3/50; C01B 3/34; C01B 2203/1241; C01B 2203/86; C10K 1/005; C10L 3/104; C10L 2200/0469; C10L 2290/26; B01D 53/047; B01D 2257/504
See application file for complete search history.

(56) References Cited

U.S. PATENT DOCUMENTS

| | | |
|---|---|---|
| 3,105,811 A | 10/1963 | Engel |
| 4,372,856 A | 2/1983 | Morrison |
| 6,503,298 B1 | 1/2003 | Monzyk et al. |
| 7,014,768 B2 | 3/2006 | Li et al. |
| 7,332,146 B1 | 2/2008 | Huang et al. |
| 7,691,182 B1 | 4/2010 | Muradov et al. |
| 7,794,690 B2 | 9/2010 | Abatzoglou et al. |
| 7,931,888 B2 | 4/2011 | Drnevich et al. |
| 7,951,296 B2 | 5/2011 | Williams |
| 7,972,082 B2 | 7/2011 | Augenstein et al. |
| 8,021,464 B2 | 9/2011 | Gauthier et al. |
| 8,057,773 B2 | 11/2011 | MacArthur et al. |
| 8,137,422 B2 | 3/2012 | Licht et al. |
| 8,268,044 B2 | 9/2012 | Wright et al. |
| 8,460,630 B2 | 6/2013 | Niitsuma et al. |
| 8,470,567 B2 | 6/2013 | Facey et al. |
| 8,475,566 B2 | 7/2013 | Find |
| 8,496,908 B1 | 7/2013 | Genkin et al. |
| 8,658,026 B2 | 2/2014 | Foody et al. |
| 8,673,056 B2 | 3/2014 | De Bas et al. |
| 8,673,135 B2 | 3/2014 | Colyar et al. |
| 8,679,439 B2 | 3/2014 | Randhava et al. |
| 8,753,854 B2 | 6/2014 | Foody |
| 8,852,456 B2 | 10/2014 | Valentin et al. |
| 8,900,546 B2 | 12/2014 | Van De Graaf et al. |
| 8,916,735 B2 | 12/2014 | McAlister |
| 8,945,373 B2 | 2/2015 | Foody |
| 8,974,669 B2 | 3/2015 | Del Porto |
| 8,980,211 B2 | 3/2015 | Timmins |
| 8,987,175 B2 | 3/2015 | Van Den Berg et al. |
| 9,028,794 B2 | 5/2015 | Darde et al. |
| 9,038,435 B2 | 5/2015 | Wang |
| 9,040,271 B2 | 5/2015 | Foody |
| 9,045,337 B2 | 6/2015 | Kuku |
| 9,108,894 B1 | 8/2015 | Foody et al. |
| 9,163,180 B2 | 10/2015 | Marion et al. |
| 9,163,188 B2 | 10/2015 | Forsyth et al. |
| 9,381,493 B2 | 7/2016 | Kirk et al. |
| 9,506,605 B2 | 11/2016 | Paget et al. |

(Continued)

FOREIGN PATENT DOCUMENTS

| | | |
|---|---|---|
| AU | 2020100873 A4 | 7/2020 |
| AU | 2021102128 A4 | 9/2021 |

(Continued)

OTHER PUBLICATIONS

Dinca, et al., "$CO_2$ Capture from Syngas Generated by a Biomass Gasification Power Plant with Chemical Absorption Process", Energy (2018).

Wismann, et al., "Electrified methane reforming: a compact approach to greener industrial hydrogen production", Science (2019), 364 (6442), 756-759.

Adair, Blake, "Ammonia: Transitioning to Net-Zero Future", Nutrien (2022).

(Continued)

*Primary Examiner* — Timothy C Vanoy

(74) *Attorney, Agent, or Firm* — Knobbe Martens Olson & Bear LLP

(57) ABSTRACT

A process and/or system for producing fuel that includes providing biogas, removing carbon dioxide from the biogas, transporting the upgraded biogas to a hydrogen plant; providing the transported upgraded biogas and fossil-based natural gas as feedstock for hydrogen production. The carbon intensity of the fuel is less than 11 g$CO_2$-eq/MJ, at least in part because carbon dioxide removed from the biogas and carbon dioxide from hydrogen production is captured and stored.

23 Claims, 4 Drawing Sheets

(56) References Cited

U.S. PATENT DOCUMENTS

| | | |
|---|---|---|
| 9,701,535 B2 | 7/2017 | Iaquaniello et al. |
| 9,816,035 B2 | 11/2017 | Lehoux et al. |
| 9,963,665 B2 | 5/2018 | Feldmann |
| 10,093,540 B2 | 10/2018 | Foody |
| 10,106,746 B2 | 10/2018 | Boon et al. |
| 10,228,131 B2 | 3/2019 | Merritt, Jr. |
| 10,302,357 B2 | 5/2019 | Hernandez et al. |
| 10,414,649 B2 | 9/2019 | Denton et al. |
| 10,421,663 B2 | 9/2019 | Foody |
| 10,760,024 B2 | 1/2020 | Foody et al. |
| 10,557,338 B2 | 2/2020 | Rhodes et al. |
| 10,577,248 B2 | 3/2020 | Haper, Jr. |
| 10,723,621 B2 | 7/2020 | Foody |
| 10,927,008 B2 | 2/2021 | Raaheim et al. |
| 10,981,784 B2 | 4/2021 | Foody |
| 11,168,339 B1 | 9/2021 | Stepany et al. |
| 11,204,271 B2 | 12/2021 | Williams et al. |
| 11,293,035 B2 | 4/2022 | Ludtke et al. |
| 11,299,686 B2 | 4/2022 | Foody et al. |
| 2003/0011141 A1 | 6/2003 | Branson |
| 2004/0111968 A1 | 6/2004 | Day et al. |
| 2006/0207178 A1 | 9/2006 | Hsu |
| 2007/0295593 A1* | 12/2007 | Martinez ............... C01B 3/08 |
| | | 204/157.43 |
| 2008/0159938 A1 | 7/2008 | Mauthner et al. |
| 2008/0262701 A1 | 10/2008 | Williams et al. |
| 2008/0280338 A1 | 11/2008 | Hall et al. |
| 2009/0162914 A1 | 6/2009 | Offerman et al. |
| 2009/0255181 A1 | 10/2009 | Rhinesmith et al. |
| 2010/0015680 A1 | 1/2010 | Van Groenestijn et al. |
| 2010/0047160 A1 | 2/2010 | Allam |
| 2010/0071429 A1 | 3/2010 | Von Nordenskjold |
| 2010/0076238 A1 | 3/2010 | Brandvold et al. |
| 2010/0158792 A1 | 6/2010 | Drnevich et al. |
| 2010/0205863 A1 | 8/2010 | Biollaz et al. |
| 2010/0228067 A1 | 9/2010 | Peterson et al. |
| 2010/0297749 A1 | 11/2010 | Aravanis et al. |
| 2011/0158858 A1 | 6/2011 | Alves Ramalho Gomes |
| 2011/0175032 A1 | 7/2011 | Gunther |
| 2011/0226997 A1 | 9/2011 | Goruney et al. |
| 2011/0229404 A1 | 9/2011 | Guo et al. |
| 2011/0305627 A1* | 12/2011 | Gupta ................... C01B 3/384 |
| | | 423/655 |
| 2012/0058045 A1 | 3/2012 | Beckman et al. |
| 2012/0165581 A1 | 6/2012 | Dupassieux et al. |
| 2012/0270119 A1 | 10/2012 | Raaheim et al. |
| 2012/0291351 A1 | 11/2012 | Bool et al. |
| 2013/0023707 A1 | 1/2013 | Keefer et al. |
| 2013/0097929 A1 | 4/2013 | Pham et al. |
| 2013/0161235 A1 | 6/2013 | Foody |
| 2013/0164806 A1 | 6/2013 | Foody |
| 2013/0345325 A1 | 12/2013 | Lecomte et al. |
| 2014/0023975 A1 | 1/2014 | Paul et al. |
| 2014/0186258 A1 | 7/2014 | Allidieres |
| 2014/0360485 A1 | 12/2014 | Saxena |
| 2015/0225233 A1 | 8/2015 | Foody |
| 2015/0376801 A1 | 12/2015 | Bairamijamal |
| 2016/0060537 A1 | 3/2016 | Hsu |
| 2016/0264418 A1 | 9/2016 | Leclerc et al. |
| 2017/0001142 A1 | 1/2017 | Rayner et al. |
| 2017/0022424 A1 | 1/2017 | Chapus |
| 2017/0051318 A1 | 2/2017 | Hakalehto |
| 2017/0130582 A1 | 5/2017 | Hsu |
| 2017/0152453 A1* | 6/2017 | Goerz ................... C10L 1/1233 |
| 2017/0158503 A1 | 6/2017 | Foody et al. |
| 2018/0079672 A1 | 3/2018 | Meyer et al. |
| 2018/0251694 A1 | 9/2018 | Foody et al. |
| 2018/0291278 A1 | 10/2018 | Jack et al. |
| 2019/0352177 A1 | 11/2019 | Denton et al. |
| 2019/0359894 A1 | 11/2019 | Heidel et al. |
| 2020/0078728 A1 | 3/2020 | Iaquaniello et al. |
| 2020/0087576 A1 | 3/2020 | Marker et al. |
| 2020/0096254 A1 | 3/2020 | Cardon et al. |
| 2020/0148964 A1 | 5/2020 | Foody et al. |
| 2020/0222874 A1 | 7/2020 | Manenti |
| 2020/0283920 A1 | 9/2020 | Bairamijamal |
| 2020/0307997 A1 | 10/2020 | Tranier |
| 2021/0078888 A1 | 3/2021 | Kanu |
| 2021/0140054 A1 | 5/2021 | Park et al. |
| 2021/0155864 A1 | 5/2021 | Foody et al. |
| 2021/0221679 A1 | 7/2021 | Foody |
| 2021/0275961 A1 | 9/2021 | Foody et al. |
| 2021/0285017 A1 | 9/2021 | Feldmann et al. |
| 2021/0317377 A1 | 10/2021 | Foody et al. |
| 2021/0324282 A1 | 10/2021 | Foody et al. |
| 2022/0042406 A1 | 2/2022 | Whikehart et al. |
| 2022/0119269 A1 | 4/2022 | Huckman et al. |
| 2022/0127211 A1 | 4/2022 | Whitmore |
| 2022/0134298 A1 | 5/2022 | Marker et al. |
| 2022/0177792 A1 | 6/2022 | Foody et al. |
| 2022/0213511 A1 | 7/2022 | Mann et al. |

FOREIGN PATENT DOCUMENTS

| | | |
|---|---|---|
| CA | 2739420 A1 | 9/2011 |
| CA | 3039567 A1 | 4/2018 |
| CN | 110776941 A | 2/2020 |
| CN | 113353886 A | 9/2021 |
| DE | 1020013011289 A1 | 1/2015 |
| EP | 2386621 A2 | 11/2011 |
| EP | 2616 530 A2 | 4/2012 |
| EP | 2724081 A2 | 12/2012 |
| EP | 2944606 A1 | 11/2015 |
| EP | 3085766 A1 | 10/2016 |
| EP | 2547619 B1 | 10/2017 |
| EP | 3484811 A1 | 1/2018 |
| EP | 4043089 A1 | 8/2022 |
| ES | 2490066 A1 | 9/2014 |
| GB | 2466554 B | 6/2010 |
| GB | 2585987 B | 10/2021 |
| GB | 2589198 B | 11/2021 |
| GB | 2592531 B | 4/2022 |
| GB | 2596675 A | 5/2022 |
| WO | WO 2003/051803 A1 | 6/2003 |
| WO | WO 2008/044929 A1 | 4/2008 |
| WO | WO 2008/109122 A1 | 9/2008 |
| WO | WO 2009/126379 A1 | 10/2009 |
| WO | WO 2010/047815 A2 | 4/2010 |
| WO | WO2010/051622 A1 | 5/2010 |
| WO | WO 2010/080407 A2 | 7/2010 |
| WO | WO 2010/124030 A1 | 10/2010 |
| WO | WO 2011/092136 A1 | 8/2011 |
| WO | WO2011/101137 A8 | 8/2011 |
| WO | WO 2012/093041 A1 | 7/2012 |
| WO | WO2013/029171 A1 | 3/2013 |
| WO | WO2013/131916 A1 | 9/2013 |
| WO | WO2014/014803 A1 | 1/2014 |
| WO | WO2015/010201 A1 | 1/2015 |
| WO | WO2016/101076 A1 | 6/2016 |
| WO | WO 2018/187716 A1 | 10/2018 |
| WO | WO 2019/129858 A1 | 7/2019 |
| WO | WO2019/185315 A1 | 10/2019 |
| WO | WO2020/010430 A1 | 1/2020 |
| WO | WO2021/003564 A1 | 1/2021 |
| WO | WO2021/035352 A1 | 3/2021 |
| WO | WO2021/035353 A1 | 3/2021 |
| WO | WO2021/062397 A1 | 4/2021 |
| WO | WO2021/110757 A1 | 6/2021 |
| WO | WO2021/142528 A1 | 7/2021 |
| WO | WO2021/175662 A1 | 9/2021 |
| WO | WO 2021/180805 A1 | 9/2021 |
| WO | WO2021/189137 A1 | 9/2021 |
| WO | WO2021/203176 A1 | 10/2021 |
| WO | WO2021/217269 A1 | 11/2021 |
| WO | WO2022/221954 A1 | 10/2022 |

OTHER PUBLICATIONS

Al-Qahtani, et al., "Uncovering the True Cost of Hydrogen Production Routes Using Life Cycle Monetisation", Applied Energy 281 (2021) 15958.

Alves et al., "Overview of Hydrogen Production Technologies from Biogas and the Applications in Fuel Cells", International Journal of Hydrogen Energy (2010) 1-11.

(56) References Cited

OTHER PUBLICATIONS

Ambrosetti et al., "A Numerical Investigation of Electrically-Heated Methane Steam Reforming Over Structured Catalysts", Frontiers in Chemical Engineering, 3 (2021) 747636.
An Introduction to Petroleum Refining and the Production of Ultra Low Sulfur Gasoline and Diesel Fuel. https://theicct.org/sites/default/files/publications/ICCT05_Refining_Tutorial_FINAL_R1.pdf. Access Date: Aug. 13, 2020.
Antonini et al, "Biomass to Hydrogen with CCS: can we go negative", https://www.sintef.no/globalassets/project/elegancy/documents/webinar3a/04-elegancy-final-presentation-ca-v2.pdf, Access date: Nov. 7, 2022.
Antonini et al, "Hydrogen Production from Natural Gas and Biomethane with Carbon Capture and Storage—A Techno-Environmental Analysis", Sustainable Energy Fuels, 4 (2020) 2967.
Arora et al. "Small-scale Ammonia Production from Biomass: A Techno-enviro-economic perspective." Industrial & Engineering Chemistry Research 55.22 (2016) 6422-6434.
Baker et al., "Hydrolysis of Cellulose Using Ternary Mixtures of Purified Cellulases," Applied Chemistry and Biotechnology, vol. 70-72 (1998) 395-403.
"Biomass with CO2 Capture and Storage (Bio-CCS) The Way Forward for Europe", European Technology Platform for Zero Emission Fossil Fuel Power Plants (2012).
"Blue Hydrogen—Groundbreaking Solutions for Hydrogen Production at Scale", Topsoe A/S, Denmark, (2022) 11 pages.
Boerrigter, "Green gas (SNG) in the Dutch Energy Infrastructure," Energy Research Centre of the Netherlands, ECN-RX-06-072 (Mar. 30, 2006) 1-11.
Boland, S., et al., GHG Emissions Reductions due to the RFS2, Life Cycle Associates, p. 1-14 (2015).
Borjesson et al. "Biogas as a resource-efficient vehicle fuel," Trends in Biotechnology, vol. 26, Issue 1 (2007) 7-13.
Brau Jean-Florian., "Production of Hydrogen for Oil Refining by Thermal Gasification of Biomass: Process Design, Integration and Evaluation", Thesis (2013) Chambers University of Technology, Sweden.
Brau et al., "Hydrogen for Oil Refining via Biomass Indirect Steam Gasification: Energy and Environmental Targets", Clean Techn. Environ. Policy (2013) 15, 501-512.
British Columbia BCBN Hydrogen Study Final Report https://www2.gov.bc.ca/assets/gov/government/ministries-organizations/zen-bcbn-hydrogen-study-final-v6.pdf, Access Date: Apr. 4, 2021.
California Executive Order S-01-07, Office of the Governor, Signed Jan. 18, 2007.
Carbolea, Animal Manures, Available Online at: www.carbolea.ul.ie/manures.php, Accessed Nov. 22, 2017.
"Clarification on Compliance with CertifHy Green Hydrogen Criteria for FCH JU Projects", www.fch.europa.eu Access date Jul. 27, 2022.
"Clean and Renewable Energy from Pulp Mill Waste Using Microsludge and Anaerobic Digestion," Paradigm Environmental Technologies Inc. (2011) 1-2.
Clean Energy Strategies for Local Governments, 7.4 Landfill Methane Utilization (Dec. 10, 2008) 1-34.
Collins, Leigh, "New Clean Hydrogen Production Tax Credit of up to $3/Kg Approved by US House, Paving Way for Cheap Green H2" Access date Jul. 26, 2022.
Cortright et al. "Hydrogen from catalytic reforming of biomass-derived hydrocarbons in liquid water," Nature, vol. 418 (2002) 964-67.
Cruz et al. "Petroleum Refinery Hydrogen Production Unit: Exergy [sic] and Production Cost Evaluation," International Journal of Thermodynamics. vol. 11, No. 4 (2008) 187-93.
Cruz et al., "Exergy Analysis of Hydrogen Production via Biogas Dry Reforming", International Journal of Hydrogen Energy, V 43, I 26, (2018) 11688-11695.
Definition of "Crude Oil", Random House Unabridged Dictionary, 2nd Ed., New York, 1993.
Energy Independence and Security Act of 2007, United States Cong. Energy Independence and Security Act of 2007, 110th Cong., Pub. L. 110-140, Enacted Dec. 19, 2007.
EPA, An Overview of Renewable Natural Gas from Biogas, Jul. 2020.
EPA, 2008b. Clean Energy Strategies for Local Governments, 7.4: Landfill Methane Utilization, Draft. Landfill Methane Outreach Program (LMOP), Climate Change Division, U.S. EPA. Dec. 10, 2008, in 34 pages. URL: https://www.epa.gov/sites/production/files/2015-12/documents/landfills.pdf.
Ewing et al., "Hydrogen on the Path to Net Zero—Costs and Climate Benefits", Pembina institute, Jul. 2020.
Ferreira-Aparicio et al., "New Trends in Reforming Technologies: from Hydrogen Industrial Plants to Multifuel Microreformers", Catalysis Reviews, 47, (2005), 491-588.
Final Assessment Report "Landfill Biogas Recovery and Utilization at the Santo Andre Municipal Sanitary Landfill Santo Andre, Brazil," Prepared under: U.S. Environmental Protection Agency Landfill Methane Outreach Program (2008) 1-31.
Full et al., A New Perspective for Climate Change Mitigation—Introducing Carbon-Negative Hydrogen Production from Biomass with Carbon Capture and Storage (HYBECCS), Sustainability (2021) 13 4026.
Gencer, Emre, et al. "Sustainable Production of Ammonia Fertilizers from Biomass." Biofuels, Bioproducts and Biorefining 14.4 (2020) 725-733.
Ghavam et al. "Sustainable Ammonia Production Processes." Frontiers in Energy Research 9 (2021) 34.
Gruia, Practical Advances in Petroleum Processing, vol. 1, Ed. By Chang S. Hsu and Paul R. Robinson, Springer, New York, Chapter 8, "Recent Advances in Hydrocracking" (2006) 219-55.
Guidance for the Certification of Co-Processing. Available online at: https://www.iscc-system.org/wp-content/uploads/2017/02/ISCC-Guidance-Document-203-01_Co-processing-requirements.pdf. Access date: Aug. 7, 2020.
Hakawati et al., "What is the Most Energy Efficient Route for Biogas Utilization: Heat, Electricity, or Transport?", Applied Energy 206 (2017) 1076-1087.
Hengeveld et al., "When Does Decentralized Production of Biogas and Centralized Upgrading and Injection into the Natural Gas Grid Make Sense", Biomass and Bioenergy, 67 (2014) 363-371.
Hidalgo, Maria, "Biomethane and Biohydrogen: the Future of Energy is Here", CARTIF Blog, Energy and Environment, Mar. 22, 2021, Access Date: Feb. 17, 2022.
Hovland, Jon, "Compression of Raw Biogas—A Feasibility Study", Report No. 2217020-1 (2017).
Howorth et al., "How Green is Blue Hydrogen", Energy Sci. Eng. (2021) 9 1676-1687.
"Hydrogen Strategy for Canada Seizing the Opportunities for Hydrogen" Access date Jan. 27, 2022.
IEAGHG Technical Review 2017-TR2, Feb. 2017. Techno-Economic Evaluation of SMR Based Standalone (Merchant) Hydrogen Plant with CCS. https://ieaghg.org/exco_docs/2017-02.pdf.
IEAGHG Technical Review 2017-TR3, Mar. 2017. Reference data and Supporting Literature Reviews for SMR based Hydrogen Production with CCS. https://ieaghg.org/publications/technical-reports/reports-list/10-technical-reviews/778-2017-tr3-reference-data-supporting-literature-reviews-for-smr-based-hydrogen-production-with-ccs.
Increasing Renewable Content with the Mass Balance Approach. https://www.nnfcc.co.uk/files/mydocs/Mass%20Balance.pdf. Access date: Jan. 18, 2022.
Jechura, John, Hydroprocessing: Hydrotreating & Hydrocracking. Chapters 7 & 9. Colorado School of Mines (2018). https://inside.mines.edu/~jjechura/Refining/08_Hydroprocessing.pdf.
Jesper et al. "Bio-SNG Potential Assessment: Denmark 2020," Riso National Laboratory for Sustainable Energy, Riso-R-1754 (Nov. 2010) 1-85.
Krich et al. Biomethane from Dairy Waste, "A Sourcebook for the Production and Use of Renewable Natural Gas in California" (Jul. 2005) 66-67 and 81-106.

(56) References Cited

OTHER PUBLICATIONS

Kurokawa et al., "Energy-Efficient Distributed Carbon Capture in Hydrogen Production from Natural Gas", Energy Procedia 4 (2011) 674-680.
Latvala, "Using Biogas in the Production of Liquid Transport Fuels as Hydrogen Source," Second Nordic Biogas Conference, Malmo, Sweden (2008) 1-13.
Marcoberardino et al., "Green Hydrogen Production from Raw Biogas: A Techno-Economic Investigation of Conventional Processes Using Pressure Swing Adsorption Unit", Processes 6 (2018) 19.
McPhail et al., The Renewable Identification System and U.S. Biofuel Mandates, USDA, BIO-03, Nov. 2011.
Mezei, "Options for Upgrading Digester Biogas to Pipeline Quality," Flotech Services (2010) 1-15.
Milbrandt et al., "Biogas and Hydrogen Systems Market Assessment", National Renewable Energy Laboratory (NREL). Technical Report NREL/TP-6A20-63596, Mar. 2016.
Milne et al. "Hydrogen from Biomass State of the Art and Research Challenges." National Renewable Energy Laboratory, A Report for the International Energy Agency Agreement on the Production and Utilization of Hydrogen Task 16, Hydrogen from Carbon-Containing Materials (2002) 1-78.
Mozaffarian et al. "Green Gas (SNG) Production by Supercritical Gasification of Biomass," Energy Research Centre of the Netherlands, ENC-C-04-081, (Nov. 2004), 1-71.
Muradov et al., "Hydrogen production by catalytic processing of renewable methane-rich gases", Int. J. of Hydrogen Energy, 33, (2008) 2033-2035.
Najafpour et al., "Hydrogen as clean fuel via continuous fermentation by anaerobic photosynthetic bacteria, Rhodospirillum rubrum," African Journal of Biotechnology vol. 3, Issue 10 (2004) 503-7.
Naqvi, Syed, "Hydrogen Production", PEP Report 32C, SRI Consulting (2007).
"Natural Gas Processing: The Crucial Link Between Natural Gas Production and Its Transportation to Market," Energy Information Administration, Office of Oil and Gas (2006) 1-11.
Ni, et al., "An Overview of Hydrogen Production from Biomass", Fuel Processing Technology 87 (2006) 461-472.
Oni et al., "Comparative Assessment of Blue Hydrogen from Steam Methane Reforming, Autothermal Reforming, and Natural Gas Decomposition Technologies for natural gas-producing regions", Energy Conversion and Management 254 (2022) 115245.
Parkinson et al., "Hydrogen Production using Methane: Techno-Economics of Decarbonizing Fuels and Chemicals", International Journal of Hydrogen Energy, 43 (2018) 2540.
"Part II—Environmental Protection Agency—40 CFR Part 80 Regulation of Fuels and Fuel Additives: Changes to Renewable Fuel Standard Program; Final Rule", Federal Register, vol. 75(58), Mar. 26, 2010, in 236 pages. URL: https://www.gpo.gov/fdsys/pkg/FR-2010-03-26/pdf/2010-3851.pdf.
Prospects of Hydrogen from Biomass, IEA Hydrogen Implementing Agreement, Annex 16, Subtask B, Final Report, (2006) 1-69.
Rapier, Robert "Estimating the Carbon Footprint of Hydrogen Production", Forbes, Jun. 6, 2020.
Rau et al., "Production of Hydrogen by Autothermal Reforming of Biogas", Energy Procedia 120 (2017) 294-301.
Regalbuto, "An NSF perspective on next generation hydrocarbon biorefineries," Computers and Chemical Engineering 34 (2010) 1393-1396.
Robinson et al., "Hydrotreating and Hydrocracking: Fundamentals", Practical Advances in Petroleum Processing, vol. 1, Ed. by Chang S. Hsu and Paul R. Robinson, Springer, New York, Chapter 7 (2006) 177-218.
RTFO Guidance Part One Process Guidance. 2020.
RTFO Guidance Part One Process Guidance. 2018.
Salary, et al., "Design of Oil Refineries Hydrogen Network Using Process Integration Principles", Iran. J. Chem. Chem. Eng., vol. 27, No. 4, (2008), 49-64.
Sanchez et al., "Biomass Based Sustainable Ammonia Production", 2019 AIChE Annual Meeting. AIChE, 2019.
Santos, Stanley, "Understanding the Potential of CCS in Hydrogen Production", Process Industry CCS Workshop (2015).
Schanbacher, "Anaerobic Digestion: Overview and Opportunities," Waste to Energy Workshop: Advances and Opportunities for Ohio's Livestock and Food Processing Industries, OARDC (Apr. 7, 2009) 1-28.
Schill, Susanne, "Iowa to Get First Biomass-to-Ammonia Plant", https://biomassmagazine.com/articles/2613/iowa-to-get-first-biomass-to-ammonia-lant/#:~:text=SynGest%20lnc.%20has%20secured%20a,deploy%20in%20its%20first%20plant., Access date: Feb. 17, 2022.
Schimmel et al., "Determining the renewability of co-processed fuels; Final Report", ECOFYS, Apr. 2018.
Serrano-Ruiz et al. "Catalytic routes for the conversion of biomass into liquid hydrocarbon transportation fuels," Energy & Environmental Science, 4 (2011) 83-99.
Shiga et al. "Large-Scale Hydrogen Production from Biogas," International Journal of Hydrogen Energy, vol. 23, No. 8 (1998) 631-40.
Show et al., "Design of Bioreactors for Biohydrogen production", Journal of Scientific & Industrial Research, vol. 67 (2008), pp. 941-949.
Spath et al. "Life Cycle Assessment of Hydrogen Production via Natural Gas Steam Reforming," NREL/TP-570-27637 (2000) 1-24.
Stavrakas et al., "Striving Towards the Deployment of Bio-energy with Carbon Capture and Storage (BECCS): A review of Research Priorities and Assessment Needs", Sustainability 2018, 10, 2206.
Streb et al., "Novel Adsorption Process for Co-Production of Hydrogen and CO2 from a Multicomponent Stream—Part 2: Application to Steam Methane Reforming and Autothermal Reforming Gases", Ind. Eng. Chem. Res. 59 (2020) 10093-10109.
Sun, et al., "Selection of Appropriate Biogas Upgrading Technology—a Review of Biogas Cleaning, Upgrading and Utilisation", Renewable and Sustainable Energy Reviews 51 (2015) 521-532.
Sun, et al., "Updates of Hydrogen Production from SMR Process in GREET". 2019.
Taylor, R., et al., "Options for a UK low carbon hydrogen standard: Final Report", Department for Business, Energy & Industrial Strategy, E4tech, May 2021.
"The Role of Biogas & RNG in Hydrogen Production & Decarbonization", BayoTech (2020).
Transportation Fuels from Biomass via IH2 Technology, IEA Bioenergy Conference, 2012. 1-25.
Union Calendar No. 94, 117th Congress 1st Session, H.R. 5376 (Report No. 117-130) (2021).
U.S. Climate Change Technology Program—Technology Options for the Near and Long Term, Methane Emissions from Energy and Waste, "Conversion of Landfill Gas to Alternative Uses," section 4.1.2 (2003) 153-155.
Van Der Drift, "SNG: A New Biomass-Based Energy Carrier," Energy Research Centre of the Netherlands (Apr. 23, 2006) 1-21.
Van Der Meijden et al. "Production of bio-methane from woody biomass," Energy Research Centre of the Netherlands, ECN-M-09-086, (Jun. 2009) 1-8.
Wang, "Low Carbon Steam Reforming-Based Hydrogen Production", https://www.gasliquids.com/wp-content/uploads/2020_Hydrogen-Production-Using-Steam-Methane-Reforming.pdf. Access date: Feb. 6, 2021.
Wang et al., The Life-Cycle Analysis of Petroleum Fuels and Biofuels with GREET. Argonne National Laboratory. Dec. 13, 2016 https://ww2.arb.ca.gov/sites/default/files/classic/fuels/lcfs/lcfs_meetings/12132016wang.pdf Access date: Jun. 2, 2020.
Worley, et al., "Biomass Gasification Technology Assessment," National Renewable Energy Laboratory (Nov. 2012) 1-358.
Yang et al., "Cost and Lifecycle Greenhouse Gas Implications of Integrating Biogas Upgrading and Carbon Capture Technologies in Cellulosic Biorefineries", Environ. Sci. Technol., 2020, 54, 12810-12819.
"Zero Carbon Hydrogen—Is it Achievable?" https://www.wsp.com/en-gb/insights/zero-carbon-hydrogen-is-it-ievable#:~:text=By%

(56) References Cited

OTHER PUBLICATIONS

20balancing%20hydrogen%20production%20between,for%20the%20decarbonisation%20of%20heat. Access date: Mar. 5, 2021.

Zhou et al., "Life-cycle Greenhouse Gas Emissions of Biomethane and Hydrogen Pathways in the European Union", https://theicct.org/publication/life-cycle-greenhouse-gas-emissions-of-biomethane-and-hydrogen-pathways-in-the-european-union/ Access Date: Nov. 7, 2022.

International Search Report and Written Opinion of PCT/CA2022/050586 dated Jun. 30, 2022.

Brown, Trevor. "Renewable Hydrogen for Sustainable Ammonia Production." Chemical Engineering Progress (2019) 47-53.

"Keeping on Pace for Net Zero: Delegated Act to specify the methodology to determine the share of biofuels and biogas used in transport resulting from biomass being processed with fossil fuels in a common process", Feedback from: Iogen Corporation in response to European Commission, "Renewable energy—Method for Calculating the Share of Renewables in the Case of Co-processing", Feedback reference F3325697 submitted on Jul. 20, 2022, https://ec.europa.eu/info/law/better-regulation/have-your-say/initiatives/12711-Renewable-energy-method-for-calculating-the-share-of-renewables-in-the-case-of-co-processing/F3325697_en, Access Date: Oct. 26, 2022.

"Hydrogen in a Low-Carbon Economy", Committee on Climate Change, Nov. 2018.

\* cited by examiner

PROCESS AND SYSTEM FOR PRODUCING LOW CARBON INTENSITY RENEWABLE HYDROGEN

TECHNICAL FIELD

The present disclosure relates to a process and/or system for producing renewable hydrogen, and in particular, to a process and/or system where carbon dioxide from the process is captured and stored.

BACKGROUND

Hydrogen is largely produced from the processing of fossil fuels. For example, hydrogen is often produced from the steam methane reforming (SMR) of natural gas or the gasification of coal. Unfortunately, the production of hydrogen from fossil fuels is associated with significant greenhouse gas (GHG) emissions, and in particular, with significant carbon dioxide ($CO_2$) emissions.

One approach to reduce the GHG emissions associated with hydrogen production is to use carbon capture and storage (CCS). CCS may, for example, involve capturing $CO_2$ emissions and storing them underground in suitable geological formations, which is also referred to as carbon sequestration. In integrating CCS with hydrogen production from fossil fuels, the fossil based $CO_2$ produced during the hydrogen production is captured and stored in order to prevent it from being released to the atmosphere, thereby reducing GHG emissions of the process (e.g., a reduction of about 80-90%).

Another approach to reduce the GHG emissions associated with hydrogen production is to use biomass rather than fossil fuels as feedstock. Such hydrogen, may for example, be produced from the gasification or pyrolysis of biomass, or by reforming biogas produced by the anaerobic digestion of biomass. Any $CO_2$ derived from biomass and produced during such processing is biogenic. As the release of biogenic $CO_2$ to the atmosphere simply returns to the atmosphere carbon that was recently fixed by photosynthesis, biogenic $CO_2$ is generally considered to be carbon neutral (e.g., its release does not result in an increase in net GHG emissions). Accordingly, in integrating CCS with hydrogen production from biomass, where biogenic $CO_2$ produced during the hydrogen production is captured and stored, there is the potential for so-called "negative emissions."

Negative emissions can be the basis for BECCS, which stands for bioenergy with carbon capture and storage. For example, in some cases, BECCS, which is a group of technologies that combine extracting bioenergy from biomass with CCS, can be viewed as a process where biomass (e.g., plants) is used to extract $CO_2$ from the atmosphere, the biomass is processed to produce bioenergy (e.g., heat, electricity, fuels) while releasing $CO_2$, and the $CO_2$ produced during the processing is captured and stored such that there is there is a transfer of $CO_2$ from the atmosphere to storage.

While BECCS is increasing discussed as a means to decrease $CO_2$ emissions and/or $CO_2$ concentrations in the atmosphere, some potential challenges that may hinder its success include 1) energy intensive biomass supply chains, 2) low energy conversion efficiencies, and/or 3) high costs (e.g., incentives and/or funding may be required). With regard to the first two points, it is generally preferable that the process provide a net energy gain (e.g., as opposed to a net energy loss, where the bioenergy provided from the process is lower than the energy put into the process) and/or that the process actually deliver net negative $CO_2$ emissions (e.g., as opposed to net positive emissions, where the $CO_2$ emissions from the bioenergy production process and CCS processes exceed the quantity of $CO_2$ captured and stored). $CO_2$ emissions from the bioenergy production process may arise from any point in the process (e.g., biomass production, transport, conversion, and/or utilization), and may for example, be attributed to non-renewable energy use within the process, waste management, and/or land use changes. With regard to the third point, for established bioenergy technologies, the cost of BECCS may be largely limited by the cost of CCS. Since the cost of CCS is typically scale sensitive, and since the capture of $CO_2$ is often considered to be one of most expensive parts of CCS, BECCS has been generally considered for applications where the $CO_2$ emissions are relatively pure and/or can be captured from a large point source.

Some potential applications of BECCS have been identified as power stations wherein biomass is combusted (e.g., where biogenic $CO_2$ generated from the combustion process is captured and stored), biogas upgrading processes (e.g., where $CO_2$ separated from the biogas captured and stored), and ethanol production processes (e.g., where $CO_2$ produced by fermentation of corn grain is captured and stored). Unfortunately, at least in part due to one or more of the challenges listed above, BECCS deployment has been slow.

In terms of hydrogen production, BECCS has been discussed for the generation of hydrogen from the gasification of biomass. Gasification is a process that converts organic or fossil-based carbonaceous materials at high temperatures (>700° C.), without combustion, with a controlled amount of oxygen and/or steam into syngas (i.e., a gas mixture primarily composed of carbon monoxide (CO) and $H_2$ and sometimes $CO_2$). The gasification of biomass, including waste, is an evolving technology for producing hydrogen. In terms of BECCS it has the advantage that it is relatively simple, can be conducted on relatively large scale, and is generally configured such that all of the $CO_2$ produced during the gasification is collected from one point source. Unfortunately, it may require some preprocessing of the feedstock (e.g., drying, grinding, etc.), may require treatment of the syngas to remove contaminants and/or reduce particulate matter emissions, and/or may require a large land footprint (e.g., for on-site storage of feedstock).

The reforming of biogas for hydrogen production has some advantages over the gasification of biomass, however, in terms of BECCS it is generally more complicated. First, raw biogas is generally regarded as low-quality fuel, which can require upgrading prior to hydrogen production. While biogas upgrading is a proven technology, it can be energy intensive and/or the cost can be a significant deterrent (e.g., in many countries, only a small share of overall biogas output is upgraded, with the remainder used in power generation, co-generation, and/or heat for buildings). Second, biogas plants (i.e., where biogas is upgraded) are often small and located close the source of biogas (e.g., remote locations). The small scale and/or distributed nature typical of biogas plants can make hydrogen production and/or CCS more challenging (e.g., both can be scale sensitive and/or energy intensive). In addition, such processes involve at least two conversions, namely, biomass to upgraded biogas and upgraded biogas to hydrogen, and thus the process is more complicated than the direct gasification of biomass. As a result, the resulting hydrogen may have net positive CO2 emissions.

SUMMARY

The present disclosure relates to a novel approach to produce renewable hydrogen from biogas, wherein the renewable hydrogen has a negative carbon intensity (CI). In particular, the present disclosure relates to a process(es)/system(s) wherein biogas is upgraded, the upgraded biogas is transported to at least one hydrogen plant, and carbon dioxide from both the biogas upgrading and the hydrogen production is captured and stored. The renewable hydrogen of the present invention can be used for many applications that are known in the art, e.g., for producing fuel, chemical product, fuel or chemical intermediates, or any combination thereof using the renewable hydrogen. For example, in certain embodiments, processes of the instant disclosure produce fuel (e.g., one or more fuels such as hydrogen, gasoline, diesel, jet fuel, methanol, ethanol, etc.), chemical product (e.g., methanol, ammonia, fertilizer, etc.), or intermediates (e.g., methanol, hydrogen, ammonia, ethanol, etc.), and include one or more steps wherein biogas is upgraded, the upgraded biogas is transported to fuel/product production, and carbon dioxide from both the biogas upgrading and the hydrogen production is captured and stored.

Advantageously, in capturing $CO_2$ at multiple stages in the process, the $CO_2$ capture process at each stage can be optimized for that stage in the process (e.g., bioenergy process), and/or a greater quantity of $CO_2$ can be stored (e.g., relative to capturing $CO_2$ from only one stage). Further advantageously, since the biogas is transported after it is upgraded, the distance between the biogas plant and the hydrogen plant can be increased (e.g., which can increase the number of potential biogas plants that can provide upgraded biogas for the hydrogen production). Accordingly, the present disclosure defies one or more common assumptions for BECCS projects (i.e., that the distance between the biomass source and the bioenergy production should be limited and/or that it is preferable to capture $CO_2$ derived from the biomass from a single, relatively large, point source), while still yielding renewable hydrogen having a negative CI.

In accordance with one aspect of the instant invention there is provided a process for producing fuel, the fuel selected from renewable hydrogen and fuel produced from renewable hydrogen, the process comprising: providing biogas, the biogas comprising methane and carbon dioxide; removing at least 50% of the carbon dioxide from the biogas, thereby producing upgraded biogas; transporting the upgraded biogas to a hydrogen plant; processing the upgraded biogas at the hydrogen plant to produce syngas, the processing comprising providing the transported upgraded biogas as feedstock for methane reforming, the syngas comprising carbon dioxide and hydrogen; and purifying at least one of the syngas or a stream derived from the syngas to produce a hydrogen product comprising renewable hydrogen, and providing a quantity of the renewable hydrogen for at least one of (i) use as a fuel or (ii) producing a fuel, wherein the process further comprises: capturing and storing a first quantity of carbon dioxide, the carbon dioxide in the first quantity removed from the biogas; and capturing and storing a second quantity of carbon dioxide, the carbon dioxide in the second quantity removed from at least one of (i') the syngas or (ii') a stream at least partially derived from the syngas, wherein the quantity of renewable hydrogen has a carbon intensity less than 0 $gCO_2$-eq/MJ, and wherein the carbon intensity is dependent on steps a) and b).

In accordance with one aspect of the instant invention there is provided a process for producing renewable hydrogen, the process comprising: providing biogas, the biogas comprising methane and carbon dioxide; removing at least 50% of the carbon dioxide from the biogas, thereby producing upgraded biogas; providing the upgraded biogas for transport; providing the transported upgraded biogas as feedstock for methane reforming, thereby producing syngas, the processing comprising the syngas comprising carbon dioxide and hydrogen; and purifying a stream selected from the syngas and a stream derived from the syngas to produce a hydrogen product gas comprising renewable hydrogen, and providing a quantity of the renewable hydrogen, wherein the process further comprises: capturing and storing a first quantity of carbon dioxide, the carbon dioxide in the first quantity removed from the biogas; and capturing and storing a second quantity of carbon dioxide, the carbon dioxide in the second quantity removed from at least one of (i') the syngas or (ii') a stream at least partially derived from the syngas, wherein the second quantity of carbon dioxide comprises at least 50% of the carbon dioxide produced from the feedstock from the methane reforming, and wherein the quantity of renewable hydrogen has a carbon intensity less than 0 $gCO_2$-eq/MJ, and wherein the carbon intensity is dependent on steps a) and b).

In accordance with one aspect of the instant invention there is provided a process for producing renewable hydrogen having low carbon intensity, the process comprising: providing biogas, the biogas comprising methane and carbon dioxide; processing the biogas in a biogas upgrading process to produce upgraded biogas, the biogas upgrading process removing at least 50% of the carbon dioxide from the biogas; providing the upgraded biogas for transport; producing hydrogen from a hydrogen production process, a feedstock for the hydrogen production process comprising the upgraded biogas, the hydrogen production process comprising subjecting the feedstock to methane reforming to produce syngas comprising carbon dioxide and hydrogen, and purifying a stream selected from the syngas and a stream derived from the syngas to produce a hydrogen product gas comprising renewable hydrogen, wherein the process further comprises: capturing and storing a first quantity of carbon dioxide, the carbon dioxide in the first quantity removed from the biogas; and capturing and storing a second quantity of carbon dioxide, the carbon dioxide in the second quantity removed from at least one of (i') the syngas or (ii') a stream at least partially derived from the syngas, and wherein the renewable hydrogen has a carbon intensity dependent on steps a) and b).

In accordance with one aspect of the instant invention there is provided a process for producing renewable hydrogen having low carbon intensity, the process comprising: providing biogas produced from a biogas production process, the biogas comprising methane and carbon dioxide, the biogas production process producing digestate; processing the biogas in a biogas upgrading process to produce upgraded biogas, the biogas upgrading process removing at least 50% of the carbon dioxide from the biogas; producing hydrogen from a hydrogen production process, a feedstock for the hydrogen production process comprising the upgraded biogas, the biogas upgrading process and the hydrogen production process conducted at different geographical locations, the hydrogen production process comprising subjecting the feedstock to methane reforming to produce syngas comprising carbon dioxide and hydrogen, and purifying a stream selected from the syngas and a stream derived from the syngas to produce hydrogen comprising renewable hydrogen, wherein the process further comprises: capturing and storing a first quantity of carbon from the biogas production process, the biogas upgrading process, or a combination thereof; capturing and storing a second quantity of carbon from at least one of (i') the syngas or (ii') a stream at least partially derived from the syngas, the second quantity of carbon comprising carbon dioxide, and wherein the renewable hydrogen has a carbon intensity dependent on steps a) and b)).

In accordance with one aspect of the instant invention there is provided a process for producing renewable hydrogen having low carbon intensity, the process comprising: producing hydrogen from a hydrogen production process, a feedstock for the hydrogen production process comprising upgraded biogas, the upgraded biogas produced in a process comprising subjecting biomass to an anaerobic digestion, thereby producing biogas and digestate, the biogas comprising methane and carbon dioxide, subjecting the biogas to biogas upgrading, thereby removing at least 50% of carbon dioxide from the biogas and producing upgraded biogas, transporting the upgraded biogas, and providing carbon containing material derived from the biomass for storage as part of a first carbon capture and storage process, the carbon containing material comprising carbon dioxide from the biogas, carbon containing material obtained or derived from the digestate, or a combination thereof, the hydrogen production process comprising subjecting the feedstock to methane reforming to produce syngas comprising carbon dioxide and hydrogen, purifying a stream selected from the syngas and a stream derived from the syngas to produce hydrogen comprising renewable hydrogen, and providing carbon dioxide produced from hydrogen production for storage as part of a second carbon capture and storage process, wherein a carbon intensity of the renewable hydrogen is reduced as a result of steps (iv) and (c).

DETAILED DESCRIPTION

Figure 1:
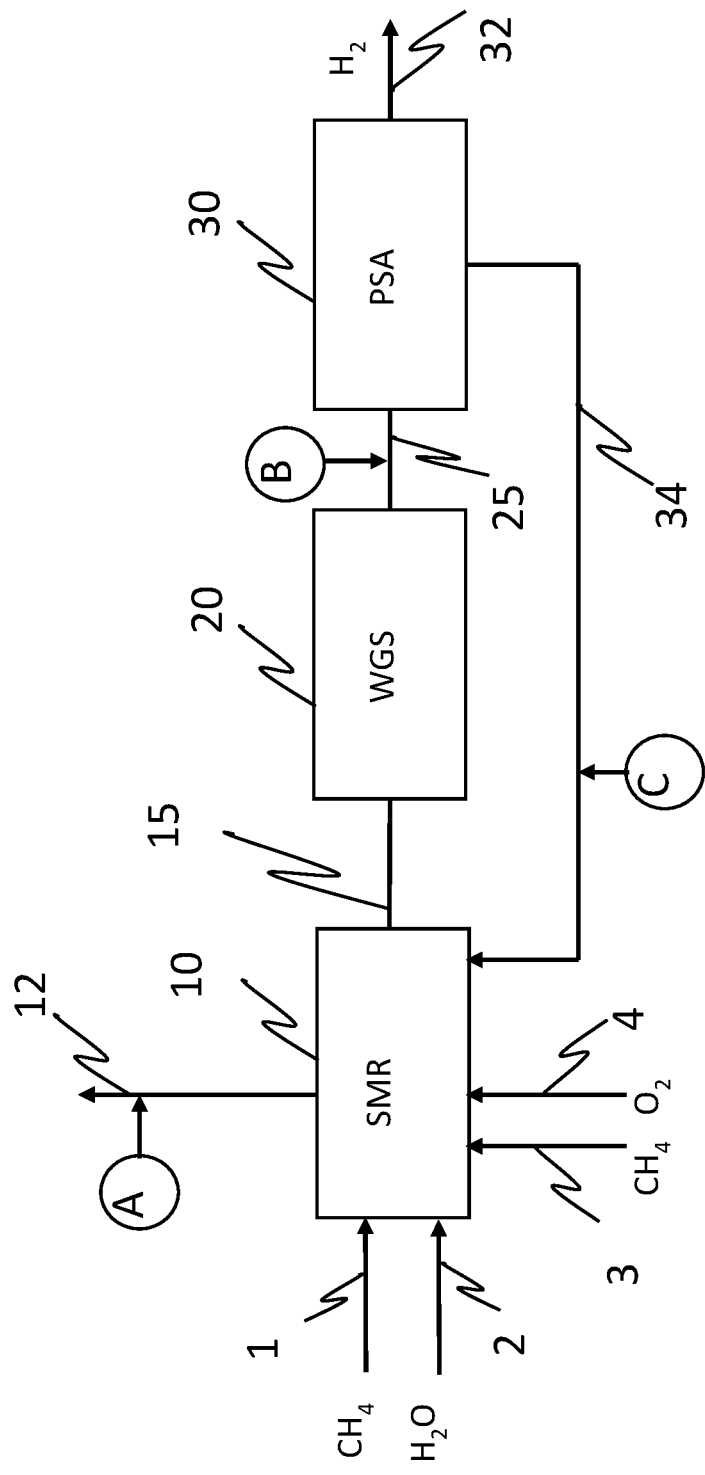
FIG. 1 is a simplified process flow diagram of one embodiment of an SMR based hydrogen plant.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, or the separating of components by the "removal" or "removing" of one component from another, those skilled in the art will understand that the order of addition/removal is not critical (unless stated otherwise). The terms "remove", "removing", and "removal", with reference to one or more impurities, contaminants, and/or constituents of biogas, includes partial removal. The terms "cause" or "causing", as used herein, may include arranging or bringing about a specific result (e.g., a withdrawal of a gas), either directly or indirectly, or to play a role in a series of activities through commercial arrangements such as a written agreement, verbal agreement, or contract. The term "associated with", as used herein with reference to two elements (e.g., a fuel credit associated with the transportation fuel), is intended to refer to the two elements being connected with each other, linked to each other, related in some way, dependent upon each other in some way, and/or in some relationship with each other. The terms "first", "second", etc., may be used to distinguish one element from another, and these elements should not be limited by these terms. The term "plurality", as used herein, refers to two or more. The term "providing" as used herein with respect to an element, refers to directly or indirectly obtaining the element and/or making the element available for use. The terms "upstream" and "downstream", as used herein, refer to the disposition of a step/stage in the process with respect to the disposition of other steps/stages of the process. For example, the term upstream can be used to describe to a step/stage that occurs at an earlier point of the process, whereas the term downstream can be used to describe a step/stage that occurs later in the process. Unless defined otherwise, all technical and scientific terms used herein have the same meanings as commonly understood by one of ordinary skill in the art.

The term "biomass", as used herein, refers to organic material originating from plants, animals, or micro-organisms (e.g., including plants, agricultural crops or residues, municipal wastes, and algae). Biomass is a renewable resource, which can be naturally replenished on a human timescale, and which can be used to produce bioenergy and/or biofuels (e.g., biogas).

The term "biogas", as used herein, refers to a gas mixture that contains methane produced from biomass. While biogas is predominately produced from the anaerobic digestion (AD) of biomass, it is also possible to produce biogas from the gasification of biomass. For example, the gasification of biomass may produce syngas, which may be cleaned up, and methanated. When produced from the anaerobic digestion of biomass, raw biogas typically includes methane ($CH_4$), carbon dioxide ($CO_2$), and can contain water ($H_2O$), nitrogen ($N_2$), hydrogen sulfide ($H_2S$), ammonia ($NH_3$), oxygen ($O_2$), volatile organic compounds (VOCs), and/or siloxanes, depending up its source. The term biogas, as used herein, can refer to raw biogas, cleaned biogas, or upgraded biogas.

The term "raw biogas", as used herein, refers to biogas as obtained from its source (e.g., anaerobic digester or landfill) before it is treated to remove any chemical components (e.g., $CO_2$, $H_2O$, $H_2S$, $O_2$, $NH_3$, VOCs, siloxanes, and/or particulates). Raw biogas can be subjected to biogas cleaning to produce cleaned biogas or subjected to biogas upgrading to produce upgraded biogas.

The term "biogas cleaning", as used herein refers to a process where biogas (e.g., raw biogas) is treated to remove one or more components (e.g., $H_2O$, $H_2S$, $O_2$, $NH_3$, VOCs, siloxanes, and/or particulates), but does not remove a significant amount of $CO_2$ and/or $N_2$ (e.g., the calorific value of the biogas may not change significantly as a result of biogas cleaning).

The term "biogas upgrading", as used herein, refers to a process where biogas (e.g., raw or cleaned biogas) is treated to remove one or more components (e.g., $CO_2$, $N_2$, $H_2O$, $H_2S$, $O_2$, $NH_3$, VOCs, siloxanes, and/or particulates), wherein the treatment increases the calorific value of the biogas. For example, biogas upgrading typically includes removing $CO_2$ and/or $N_2$. Biogas upgrading, which can include biogas cleaning, produces upgraded biogas. The term "upgraded biogas", as used herein, can refer to a partially purified biogas (i.e., requires further treatment in order to meet applicable specifications) or renewable natural gas (RNG).

The term "renewable natural gas" or "RNG", as used herein, refers to biogas that has been upgraded to meet or exceed applicable natural gas pipeline specifications, meet or exceed applicable quality specifications for vehicle use (e.g., CNG specifications), and/or natural gas withdrawn from a natural gas distribution system that is associated with the environmental attributes of biogas injected into the natural gas distribution system (e.g., a gas that qualifies as RNG under applicable regulations). For example, the term RNG can refer to natural gas withdrawn from a distribution system that has been assigned environmental attributes associated with a corresponding amount of RNG, upgraded from biogas, that was injected into the natural gas distribution system. Pipeline specifications include specifications required for biogas for injection into a natural gas distribution system. Pipeline quality standards or specifications may vary by region and/or country in terms of value and units. For example, pipelines standards may require the RNG to have a $CH_4$ level that is at least 95% or have a heating value of at least $_{950}$ BTU/scf. The percentages used to quantify gas composition and/or a specific gas content, as used herein, are expressed as mol%, unless otherwise specified. More specifically, they are expressed by mole fraction at standard temperature and pressure (STP), which is equivalent to volume fraction.

The term "natural gas" or "NG", as used herein, refers a gas mixture rich in hydrocarbons, where the primary component is $CH_4$. The term "gas" or "gas mixture", as used herein, refers to a fluid that is gaseous at standard temperatures and pressures, unless indicated otherwise.

The term "environmental attributes", as used herein with regard to a specific material (e.g., biogas), refers to any and all attributes related to the material, including all rights, credits, benefits, or payments associated with the renewable nature of the material and/or the reduction in or avoidance of fossil fuel consumption or reduction in lifecycle GHG gas emissions associated with the use of the material. Some non-limiting examples of environmental attributes include verified emission reductions, voluntary emission reductions, offsets, allowances, credits, avoided compliance costs, emission rights and authorizations, certificates, voluntary carbon units, under any law or regulation, or any emission reduction registry, trading system, or reporting or reduction program for GHG gas emissions that is established, certified, maintained, or recognized by any international, governmental, or nongovernmental agency.

The terms "capturing and storing", as used herein with reference to $CO_2$, refers to capturing the $CO_2$ and storing the captured $CO_2$ to prevent the captured $CO_2$, or an equal quantity of $CO_2$ displaced physically by the captured $CO_2$, from being released to the atmosphere. Capturing the $CO_2$ can include removing $CO_2$ from a gas mixture (e.g., biogas, syngas) using any suitable separation technology, or if the $CO_2$ is relatively pure, capturing the $CO_2$ can simply refer to collecting the $CO_2$ (e.g., in a pipe). Storing the captured $CO_2$ can include sequestering it underground (e.g., trapping it in geological formations, such as saline aquifers, or using it for enhanced oil recovery (EOR)), or can include storing the captured $CO_2$ in one or more products (e.g., using the captured $CO_2$ as a resource to create valuable products such plastics, concrete, etc.). For example, "capturing and storing $CO_2$" can be part of one or more processes commonly referred to as "carbon capture and sequestration", "carbon capture and utilization" or CCU, or "carbon capture, utilization and storage" or CCUS. In most cases, capturing and storing $CO_2$ also includes compressing the captured $CO_2$ (e.g., to produce liquid $CO_2$ or for injection into a $CO_2$ distribution system) and transporting the captured $CO_2$ to storage (e.g., by vehicle and/or a $CO_2$ distribution system). As will be understood by those skilled in the art, it can be advantageous to store the captured $CO_2$ using a method recognized by the applicable regulatory authority for reducing GHG emissions and/or mitigating climate change.

The term "carbon intensity" or "CI" refers to the quantity of lifecycle GHG emissions, per unit of fuel energy, and is often expressed in grams of $CO_2$ equivalent emissions per unit of fuel (e.g., $gCO_2e/MJ$ or $gCO_2e/MMBTU$). As will be understood by those skilled in the art, CI is often determined using Lifecycle Analysis (LCA), which identifies and estimates all GHG emissions in producing a fuel/product (e.g., renewable hydrogen), from the growing or extraction of raw materials, to the production of the fuel/product, through to the end use of the fuel/product (e.g., well-to-wheel). Those skilled in the art will understand that CI values for a given fuel/product can be dependent on the LCA methodology used (e.g., as required by the applicable regulatory authority). Methodologies for calculating carbon intensities and/or lifecycle GHG emissions according to various regulatory bodies are well known in the art and can be readily calculated by those of ordinary skill in the art. The CI values recited herein are determined using the CA-GREET 3.0 model (e.g., see, https://ww2.arb.ca.gov/resources/documents/lcfs-life-cycle-analysis-models-and-documentation), unless otherwise specified.

The present disclosure relates to producing renewable hydrogen having a negative CI from biogas, which can be used as fuel, as industrial feedstock (e.g., to produce fuel, fuel intermediates, or chemical products), or in fuel cells (e.g., to generate heat and/or electricity). For example, hydrogen is commonly used in oil refining, ammonia production, methanol production, and steel production.

Raw biogas produced from the anaerobic digestion of biomass can have a significant $CO_2$ content (e.g., about 35%), which reduces the calorific value of the biogas (i.e., relative to pure methane). As a result, the use of raw and/or cleaned biogas may be limited to power generation, co-generation, or producing heat for buildings. Alternatively, raw or cleaned biogas can be upgraded (e.g., to RNG) and used as a substitute for fossil based natural gas (e.g., used as a transportation fuel in the form of compressed RNG (bio-CNG) or liquefied RNG (bio-LNG)).

As a substitute for fossil based natural gas, upgraded biogas (e.g., RNG) may be used to produce renewable hydrogen using any technology suitable for converting natural gas to hydrogen (e.g., methane reforming). Renewable hydrogen, which can be used as a fuel in gas or liquid form, is very versatile as it can be used as a fuel, converted into electricity, and/or converted to one or more fuels. For example, renewable hydrogen can power fuel cell electric vehicles (FCEVs), which emit no tailpipe emissions other than water, or can be run through a fuel cell to power the electricity grid. Alternatively, renewable hydrogen can be used to produce liquid fuels (e.g., gasoline, diesel, jet fuel) that are renewable and/or have renewable content.

Converting upgraded biogas (e.g., RNG) to renewable hydrogen by SMR is advantageous in that it exploits technology that is well established for natural gas. Unfortunately, compared to natural gas, supply of biogas may be limited, may fluctuate with the season, and/or may be from remote locations. While the relatively small scale and/or remote locations may be advantageous when the goal is to produce a grid of hydrogen refueling stations for FCEVs (e.g., where multiple geographically spaced small scale hydrogen plants can avoid transport and storage problems with hydrogen), such distributed hydrogen production cannot take advantage of economies of scale (e.g., SMR based hydrogen production is more economical when operated at a large scale), and thus is more expensive. Given the low value of raw biogas, the relatively small scale of many biogas plants, the cost of biogas upgrading, and/or the cost of SMR, it may be challenging to find facility owners willing to collect biogas and convert it to hydrogen, particularly since other uses of biogas are more economical.

It may be particularly challenging to find facility owners further willing to integrate CCS with such processes. Distributed carbon capture may be considered unfavorable compared to centralized large-scale carbon capture. For example, the cost of CCS is typically scale sensitive, and since distributed hydrogen production is generally small scale, the cost of CCS for distributed hydrogen production may be prohibitive. In addition, a lack infrastructure (e.g., $CO_2$ pipelines) and/or space-consuming $CO_2$ purification and capture equipment may be a deterrent for distributed CCS.

While large-scale CCS has been demonstrated for SMR plants that process fossil based natural gas, it is not cheap, and is not necessarily simple. For example, consider the hydrogen plant illustrated in FIG. 1. A stream of preheated natural gas 1 is desulfurized (not shown) and fed, along with steam 2, into the reactor tubes for the SMR 10, which contain the reforming catalyst. Streams of natural gas 3 and combustion air 4 are fed into the SMR burners, which provide the heat required for the endothermic reforming reaction. The syngas 15 produced from the SMR is fed to water gas shift (WGS) 20 to produce more hydrogen. The resulting syngas 25, which may also be referred to as shifted gas, is cooled (not shown) and purified using pressure swing adsorption (PSA) 30, which produces a stream enriched in hydrogen 32 and a purge stream 34. The purge stream 34, which may contain unconverted $CH_4$, $H_2$, $CO_2$, and/or CO, is fed back to SMR 10, where it is used to provide process heat for the SMR (e.g., fuel the SMR burners). More specifically, the purge stream 34 is combusted together with the stream of natural gas 3.

In the hydrogen production process illustrated in FIG. 1, there are two sources of $CO_2$, namely, $CO_2$ produced from the feedstock 1 for the SMR (e.g., $CO_2$ in the syngas 25), which can make up about 60% of the total $CO_2$ produced, and $CO_2$ produced from the fuel 3 for SMR (e.g., $CO_2$ in the flue gas 12), which can make up about 40% of the total $CO_2$ produced, depending upon the configuration of the hydrogen plant. In terms of capturing $CO_2$, there are various options of how and where the $CO_2$ may be captured, each with different energy requirements and/or yields. FIG. 1 identifies three possible options.

The first option, which is labelled A, captures $CO_2$ from the flue gas 12, and thus captures both $CO_2$ from the feedstock and $CO_2$ from the fuel (e.g., may capture up to about 90% of the total $CO_2$ produced). The second option, which is labelled B, captures $CO_2$ from the syngas 25, and thus captures only the $CO_2$ from the feedstock (e.g., about 60% of the CO2). The third option, which is labelled C, captures $CO_2$ from the purge gas 34, and thus also captures only the $CO_2$ from the feedstock. While the first option theoretically can capture more $CO_2$ from the hydrogen production, capturing carbon dioxide from the syngas 25 (e.g., using vacuum pressure swing adsorption (VPSA) or an absorption amine unit) or from the purge gas 34 (e.g., using an activated amine process) may be more technically and/or economically feasible. For example, relative to the syngas 25, the flue gas may have a relatively low $CO_2$ concentration (e.g., relatively low partial pressure) and/or may be at a lower pressure (e.g., atmospheric). In addition, the flue gas may contain $N_2$ ($N_2$-$CH_4$ separations may be more challenging than $CO_2$-$CH_4$ separations).

In general, the SMR of fossil based natural gas to produce hydrogen can produce significant GHG emissions. While cooling of the syngas can allow heat recovery back into the process (e.g., steam generation and boiler feed water preheating), thereby preventing GHG emissions that would be associated with the heat, the resulting hydrogen can still have a high CI. For example, hydrogen produced from the SMR of fossil based natural gas, which is often referred to as "grey hydrogen," may have a CI of about 100 $gCO_2e/MJ$. When CCS is integrated with the SMR of fossil based natural gas, the resulting hydrogen it is often referred to as "blue hydrogen." As will be understood by those skilled in the art, the CI of blue hydrogen is dependent on both the hydrogen production and how much of the fossil based $CO_2$ is captured and stored. For example, in the case where only the $CO_2$ from the feedstock is captured and stored (i.e., not the flue gas), blue hydrogen may have a CI of about 45 $gCO_2e/MJ$.

As discussed herein, another approach to reduce the CI of hydrogen is to use a renewable feedstock (e.g., use RNG instead of fossil based natural gas), thereby producing renewable hydrogen. The CI of renewable hydrogen produced by the SMR of RNG can be dependent on the CI of the RNG, which can be dependent upon its source. For example, compared to the CI of fossil based natural gas, which can be about 80 $gCO_2e/MJ$, RNG produced from a landfill may have a CI of about 46 $gCO_2e/MJ$, whereas RNG produced from manure may have a CI of about −271 $gCO_2e/MJ$ of $CH_4$ (e.g., as a result of avoided GHG emissions). Assuming that fossil based natural gas is used to fuel the SMR (e.g., fuel stream 3 is fossil based natural gas), the CI of renewable hydrogen produced by the SMR of landfill based RNG may be about 65 $gCO_2e/MJ$ (e.g., higher than blue hydrogen). If this process is integrated with CCS, wherein only the $CO_2$ from the feedstock is captured and stored, the renewable hydrogen may have a CI of about 11 $gCO_2e/MJ$. Such calculations are discussed in further detail with regard to Table 1. For comparative purposes, the CI of compressed $H_2$ from electrolysis run with green electricity, which can be referred to as "green hydrogen", may be less than 10 $gCO_2e/MJ$.

While a CI of about 10 $gCO_2e/MJ$ is generally preferable to 100 $gCO_2e/MJ$, it would be advantageous to provide renewable hydrogen having a lower CI, and in particular, a negative CI. In theory, the CI of renewable hydrogen produced by the SMR of RNG produced from a landfill may be able to be reach below 10 $gCO_2e/MJ$ if the $CO_2$ from the flue gas is also, or alternatively, captured. However, capturing $CO_2$ from the flue gas can be costly. Additionally, or alternatively, the CI of the renewable hydrogen produced by the SMR of RNG may reach below 10 $gCO_2e/MJ$ if the feedstock for producing the RNG is manure (e.g., $CH_4$ having a CI of about −271 $gCO_2e/MJ$). Unfortunately, biogas production from manure can be more costly and/or may be associated with a limited supply (e.g., relative to landfill gas).

The present disclosure relates to at least one process/system wherein the CI of renewable hydrogen is low as a result of capturing and storing $CO_2$ not only from the hydrogen production (e.g., from the feedstock and/or fuel) but also from the biogas upgrading. Accordingly, the renewable hydrogen can have a negative CI regardless of whether the biogas is generated from a landfill or from manure and/or whether the $CO_2$ is collected from the flue gas of the SMR. For example, consider the schematic diagram illustrated in FIG. 2.

Figure 2:
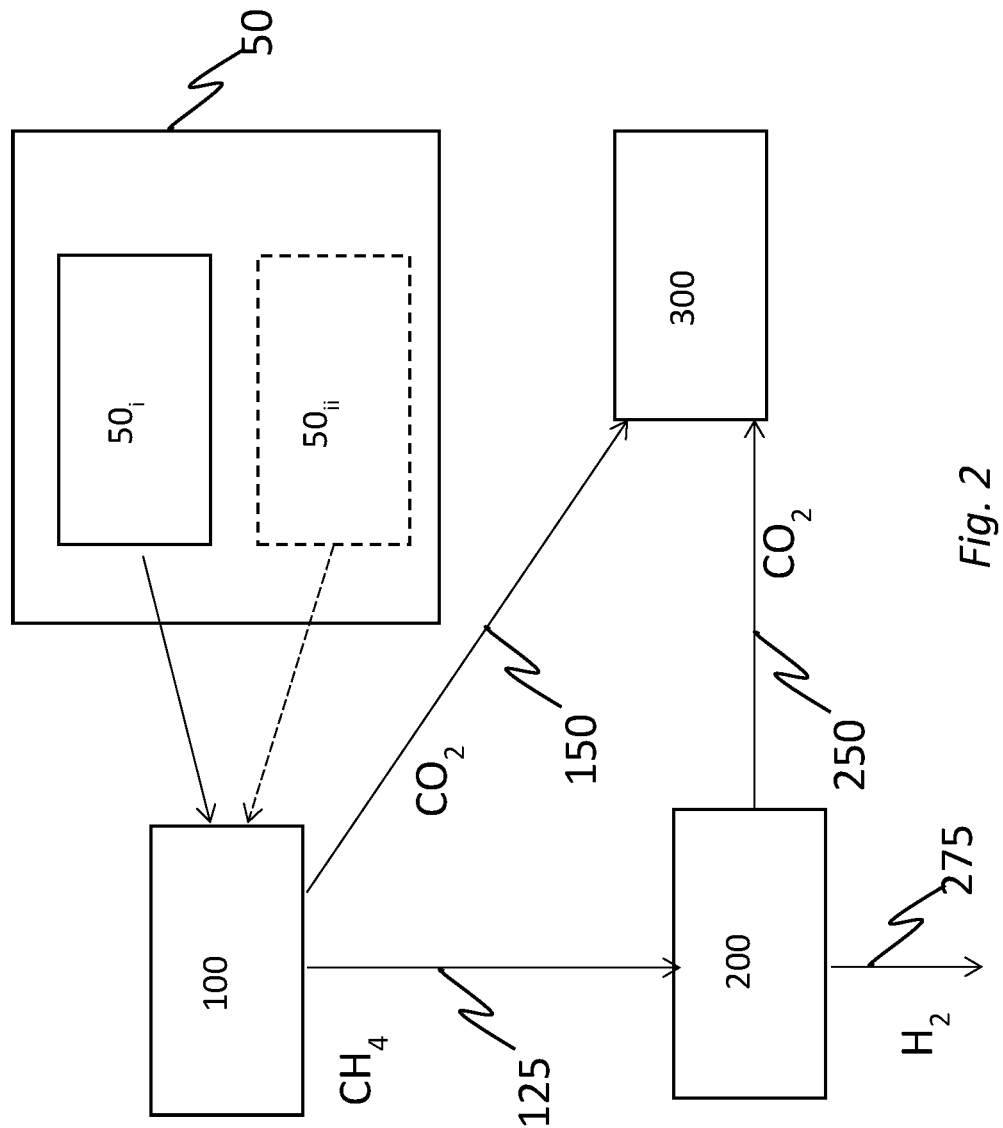
FIG. 2 is a simplified process flow diagram illustrating an embodiment wherein biogas is upgraded, the upgraded biogas is converted to hydrogen, and $CO_2$ from both the biogas upgrading and hydrogen production is captured and stored.

Referring to FIG. 2, biomass is converted to biogas at biogas production 50. Biogas production 50 provides biogas from at least one biogas source 50, (e.g., a landfill or anaerobic digester). The biogas (e.g., raw or cleaned) is subjected to biogas upgrading 100. The biogas upgrading 100 can be conducted at or near at the biogas source 50, (e.g., at a biogas plant at the landfill or farm) or can be conducted at a centralized biogas upgrading facility that also processes biogas from other biogas sources (e.g., $50_{ii}$). The upgraded biogas (e.g., RNG) 125 is transported to hydrogen production 200 (e.g., to a commercial hydrogen plant or a hydrogen plant at a fuel production facility). Hydrogen production 200 converts at least a portion of the upgraded biogas (e.g., RNG) to renewable hydrogen (e.g., via SMR). The renewable hydrogen in the $H_2$ product 275 can be used as a transportation fuel (e.g., direct combustion or in a fuel cell), used for generating electricity (e.g., in a fuel cell), and/or used as an industrial feedstock (e.g., to produce a fuel such as a transportation fuel).

At least a portion of the $CO_2$ from the biogas (e.g., generated during anaerobic digestion) 150, and at least a portion of the $CO_2$ produced from hydrogen production 250, is captured and provided for storage 300. In general, the upgraded biogas 125 may be transported to hydrogen production 200 and the $CO_2$ 150, 250 may be transported to storage 300 (if required) using any suitable mode of transportation, including transport by pipeline and/or vehicle (e.g., ship, rail car, truck). For example, in one particularly advantageous embodiment, the upgraded biogas 125 is injected into a natural gas distribution system near the biogas upgrading 100 and is withdrawn from the same natural gas distribution system for hydrogen production 200 (e.g., is transported as a fungible batch to the hydrogen plant and/or fuel production facility). In general, the $CO_2$ captured from the biogas upgrading 150 and from the hydrogen production 250 can be stored together or separately. For example, the $CO_2$ captured from the biogas upgrading 150 may be used for CCSU, while the $CO_2$ captured from the hydrogen production 250 may be used for CCS. In some embodiments, the $CO_2$ captured from the biogas upgrading 150 and from the hydrogen production 250 are transported to storage, at least in part, using one or more $CO_2$ distribution systems. For example, in one particularly advantageous embodiment, the captured $CO_2$ (e.g., 150 and/or 250) is injected into a $CO_2$ distribution system for transport and is withdrawn from the same $CO_2$ distribution system for storage (e.g., is transported as a fungible batch(es) to storage). $CO_2$ distributions systems, which typically transfer large quantities of $CO_2$ by pipeline, are increasingly used to facilitate enhanced oil recovery (EOR).

Although this process relies on at least two $CO_2$ capture steps, which are often considered to be energy-consuming steps, there are various advantages and/or synergetic benefits of using this process for producing renewable hydrogen.

For example, compare the process discussed with reference to FIG. 2 to the gasification of biomass. Biomass gasification may offer large scale centralized hydrogen production, facilitates collecting the biogenic carbon dioxide from one point source, and avoids some intermediate steps (e.g., the conversion of biomass to biogas and biogas upgrading). Nevertheless, there are challenges to hydrogen production via biomass gasification, many of which relate to the costs associated with capital equipment and biomass feedstocks. A facility producing 100 tonnes of hydrogen per day may be very large (e.g., require 1,350 dry tonnes of biomass feedstock per day), and thus may not be feasible based on regional supplies. Smaller facilities may be more feasible from a feedstock availability perspective but may drive up the capital expenditures. The cost of the biomass feedstocks can be dependent on costs for storage and transportation of the biomass, the latter of which may be dependent on the collection radius. Feedstock costs may be modest where agricultural residues can be collected and transported over short distances, but can be high when significant transport distances are involved, at least in part due to the low energy density of biomass.

Alternatively, compare the process discussed with reference to FIG. 2 to the SMR of biogas, wherein biomass is transported to a centralized processing facility that conducts the anaerobic digestion, biogas upgrading, and hydrogen production (i.e., upgraded biogas is not transported). As with the gasification of biomass, the feedstock costs for such a process can be largely dependent on the storage and transportation of the biomass. When the feedstock has a large moisture content (e.g., manure or food waste) the transportation cost may be even higher.

In contrast, in the process illustrated in FIG. 2, the upgraded biogas is transported for hydrogen production (i.e., biogas upgrading 100 and hydrogen production 200 are conducted at different locations). Transporting upgraded biogas over extended distances can be more cost efficient than transporting feedstock for anaerobic digestion and/or gasification. In particular, upgraded biogas such as RNG may be transported using any method suitable for transporting natural gas (e.g., a truck designed for transporting liquified natural gas (LNG) or compressed natural gas (CNG), the latter of which is often transported at pressures above about 3600 psig (24.8 MPa)). Transporting the upgraded biogas as bio-LNG or bio-CNG allows more MJ to be delivered per truck (e.g., relative to biomass for gasification or anaerobic digestion) and/or can increase the collection radius for the renewable feedstock. Alternatively, or additionally, the upgraded biogas can be transported by pipeline (e.g., in a natural gas distribution system such as the US natural gas grid), where it is transported as a fungible batch.

Transporting the upgraded biogas via a natural gas distribution system is particularly advantageous. In particular, it is a cost effective method that uses existing infrastructure, and depending upon the applicable regulatory agency, may have only a small penalty (cost and/or GHG emissions) for transporting the upgraded biogas over extended distances. Accordingly, the collection zone for the renewable feedstock is not limited to the area around a centralized facility conducting anaerobic digestion, biogas upgrading, and hydrogen production, but rather can include any area that provides feedstock for biogas production, where the biogas production is near the natural gas distribution system or can be economically transported to an injection point of the natural gas distribution system. This can increase the area from which the feedstock is collected, thereby making more feedstock available for the process and increasing the feasible scale of the renewable hydrogen production and/or CCS. Transporting the upgraded biogas via a natural gas distribution system also advantageously facilitates the co-processing of renewable and non-renewable feedstock (e.g., upgraded biogas and fossil-based natural gas).

Co-processing renewable and non-renewable feedstock can increase the possible scale of hydrogen production and/or CCS (e.g., biogenic and fossil $CO_2$ can be captured and stored together), can facilitate using existing hydrogen plant(s) configured to process natural gas, and/or can reduce operational complications associated with intermittent renewable feedstock supply (e.g., cold start-up times may be between about 15 and 24 hours). Accordingly, the costs of hydrogen production and/or CCS can be reduced. In addition to the economies of scale, the costs of CCS may be reduced when the hydrogen plant is in close proximity to a $CO_2$ pipeline.

Advantageously, providing multiple $CO_2$ capture steps (e.g., the disaggregation of $CO_2$ capture processes) for $CO_2$ storage allows each capture process to be optimized for that stage of the process (e.g., bioenergy process). For example, since biogas upgrading typically includes separating $CO_2$ from $CH_4$, many biogas upgrading technologies can include $CO_2$ capture, can be readily modified to include $CO_2$ capture, or may facilitate $CO_2$ capture, thereby reducing costs of at least one $CO_2$ capture step.

Further advantageously, providing multiple $CO_2$ capture steps, each at a different stage of the process, can result in the renewable hydrogen having not only a negative CI, but a CI that is not higher than $-10$ $gCO_2e/MJ$, $-20$ $gCO_2e/MJ$, $-30$ $gCO_2e/MJ$, $-40$ $gCO_2e/MJ$, $-50$ $gCO_2e/MJ$, $-60$ $gCO_2e/MJ$, or $-70$ $gCO_2/MJ$ of $H_2$. For example, consider the example where biogas having a $CH_4$ content of about 60% and a $CO_2$ content of about 40% is upgraded and subjected to SMR to produce hydrogen. Even if 100% of the $CO_2$ generated from the hydrogen production is captured and stored (i.e., from feedstock and fuel), without capturing the $CO_2$ from the biogas upgrading, a lot of the carbon from the biogas will be released to the atmosphere as $CO_2$ (e.g., 40% of the biogas on a volume basis, or about 65% of the biogas on a mass basis). While providing a zero carbon hydrogen is generally advantageous, it may be particularly advantageous if the CI is as low as possible when the hydrogen is used as a fuel or to produce a fuel, for fuel credit purposes.

Further details about the biogas production 50, the biogas upgrading 100, hydrogen production 200, capture and/or storage 300, and optional fuel production and/or fuel credits, are discussed below.

Biogas Production

In general, the biogas can be produced from any suitable biomass. For example, the biogas can be produced from the anaerobic digestion of any suitable feedstock. Anaerobic digestion, which refers to the biological breakdown of organic matter by anaerobic microorganisms, is typically conducted in anaerobic or low oxygen conditions, and may involve a series of microorganism types and processes (e.g., hydrolysis, acidogenesis, acetogenesis, and methanogenesis).

In one embodiment, the biogas is produced from the anaerobic digestion of any suitable feedstock, where the feedstock is and/or comprises: (i) an energy crop (e.g., switchgrass, sorghum, etc.); (ii) residues, byproducts, or waste from the processing of plant material in a facility, or feedstock derived therefrom (e.g., sugarcane bagasse, sugarcane tops/leaves, corn stover, etc.); (iii) agricultural residues (e.g., wheat straw, corn cobs, barley straw, corn stover, etc.); (iv) forestry material; (v) pulp and paper residues; and/or (vi) municipal waste or components removed or derived from municipal waste. In one embodiment, the feedstock for the anaerobic digestion is or includes cellulosic and/or lignocellulosic material(s).

In one embodiment, the biogas is produced from the anaerobic digestion of "organic waste." Using organic waste as the feedstock for anaerobic digestion is particularly advantageous. Organic waste, may for example, include the organic fraction of municipal solid waste (MSW), sludge from a wastewater treatment plant (WWTP), manure from a livestock farm (e.g., a dairy or swine farm), or food or yard waste collected from households, restaurants, supermarkets, food-processing companies, schools, businesses, etc. In one embodiment, the feedstock for the anaerobic digestion is manure (e.g., swine or dairy) or other farm waste, the organic fraction of MSW, or agricultural residues (e.g., straw, stover, etc.).

The composition of biogas produced from anaerobic digestion can be dependent upon the feedstock. For example, although biogas produced from anaerobic digestion generally has a $CH_4$ content between about 35% and 75% (e.g., about 60%) and a $CO_2$ content between about 15% and 65% (e.g., about 35%), the $CH_4$ content can tend towards the high end of this range when the feedstock is agricultural waste (e.g., between about 50% and 75%) and towards the low end of this range when the feedstock is the organic fraction of municipal solid waste (e.g., between about 25% and 65%). In addition to $CH_4$ and $CO_2$ biogas produced from anaerobic digestion may also include $N_2$, $H_2O$, $H_2S$, $O_2$, $NH_3$, VOCs, siloxanes, and/or particulates, in dependence upon its source. For example, biogas produced from a landfill often has a higher $N_2$ content than biogas produced in anaerobic digester. In one embodiment, the raw biogas has a $CH_4$ content between about 25% and 75% and a $CO_2$ content between about 15% and 65%, and the $CO_2$ and $CH_4$ make up at least 75% of the biogas by volume.

The anaerobic digestion of the feedstocks (e.g., solid or liquid) can be conducted in any suitable environment, including a natural environment (e.g., a landfill) or a controlled environment (e.g., an anaerobic digester). An anaerobic digester can be a holding tank, or another contained volume, such as a covered lagoon or sealed structure, configured to facilitate the breakdown of organic material by microorganisms under anaerobic or low oxygen conditions. Anaerobic digestion may be carried out in one or multiple anaerobic digesters connected in series and/or parallel, where each digester may be a single-stage or multi-stage digestion system, and/or may be designed and/or operated in a number of configurations including batch or continuous, mesophilic or thermophilic temperature ranges, and low, medium, or high rates. The term "anaerobic digester", as used herein, can refer to plurality of fluidly connected anaerobic digesters. The operation of an anaerobic digester may be dependent on nature of the organic matter fed to the anaerobic digester and/or the level of digestion required. The appropriate selection of operating parameters, including but not limited to residence time, temperature, pH, and/or the nutrients supplied, will be known to those skilled in the art.

When conducted in one or more anaerobic digesters, the anaerobic digestion of biomass also produces a potentially usable digestate. Digestate refers to the material remaining after one or more stages of the anaerobic digestion (e.g., may refer to acidogenic digestate, methanogenic digestate, or a combination thereof). Digestate can include organic material not digested by the anaerobic microorganisms, by-products of the anaerobic digestion released by the microorganisms, and/or the microorganisms themselves. For example, the digestate can include carbohydrates, nutrients (such as nitrogen compounds and phosphates), other organics, and/or wild yeasts. The composition of digestate can vary depending on the biomass from which it is derived. Digestate often has both a solid and liquid component. A common use of digestate is as a soil conditioner, where it can provide nutrients for plant growth and/or displace the use of fossil-based fertilizers. In one embodiment, the digestate is processed to provide carbon-containing material that is stored as part of CCS.

In general, the biogas can be produced from one or more sources (e.g., one or more landfills and/or anaerobic digesters). In one embodiment, the biogas is produced from a single biogas source. In one embodiment, the biogas is produced from multiple biogas sources.

Biogas Upgrading

In general, the biogas produced from the feedstock(s) is upgraded in one or more stages to provide upgraded biogas (i.e., prior to transport to hydrogen production). Biogas upgrading, which increases the calorific value of the biogas, typically provides a $CH_4$-rich gas having a $CH_4$ content of at least 90%. In one embodiment, the upgraded biogas has a $CH_4$ content of at least 90%, at least 91%, at least 92%, at least 93%, at least 94%, at least 95%, at least 96%, at least 97%, or at least at least 98%. It can be particularly advantageous to produce upgraded biogas having a $CH_4$ content that facilitates transporting the upgraded biogas as CNG, or that facilitates injection into a natural gas distribution system. In one embodiment, the biogas upgrading produces RNG. In one embodiment, the biogas upgrading produces biogas having a $CH_4$ content of at least 95%. In one embodiment, the biogas upgrading produces biogas having a heating value of at least 950 BTU/ft$^3$.

Biogas upgrading can be conducted using any suitable technology or combination of technologies that can separate $CH_4$ from one or more non-methane components in the biogas (e.g., $CO_2$, $N_2$, $H_2S$, $H_2O$, $NH_3$, $O_2$, VOCs, siloxanes, and/or particulates). For example, biogas upgrading technologies are often based on absorption, adsorption, membrane separation, and/or cryogenic separation. As will be understood by those skilled in the art, the technology used for the biogas upgrading can be dependent up the composition of the biogas and the desired purity of the upgraded biogas.

As biogas typically has a significant $CO_2$ content, biogas plants often include at least one system for separating $CH_4$ from $CO_2$. Some examples of technologies that can remove $CO_2$ from biogas include, but are not limited to, absorption (e.g., water scrubbing, organic physical scrubbing, chemical scrubbing), adsorption (e.g., pressure swing adsorption (PSA)), membrane separation (e.g., $CO_2$ selective membranes based on polyimide, polysulfone, cellulose acetate, polydimethylsiloxane), and cryogenic separation.

While some $CO_2$ removal systems may remove one or more other non-methane components in addition to $CO_2$ (e.g., $N_2$, $H_2S$, $H_2O$, $NH_3$, $O_2$, VOCs, siloxanes, and/or particulates), biogas plants often include one or more other systems (e.g., dehydration units, $H_2S$ removal units, $N_2$ rejection units, etc.). For example, some $CO_2$ removal systems require that the biogas be cleaned upstream of $CO_2$ removal (e.g., remove impurities that can negatively affect the $CO_2$ removal unit. Alternatively, or additionally, the biogas can be cleaned and/or upgraded downstream of $CO_2$ removal. In general, the non-methane components can be removed by any combination of chemical and/or physical technologies, in one or more stages. For example. $H_2O$ may be removed using a standard biogas dehumidifier, whereas $H_2S$ may be removed using a commercial $H_2S$ removal unit (e.g., based on activated carbon, molecular sieve, iron sponge, water scrubbing, NaOH washing, and/or biofilter or biotrickling filter technologies). In some cases, one stage may remove more than one non-methane component. For example. in some cases, some $H_2S$ may also be removed during the water removal step.

In general, the biogas upgrading can be conducted close to the biogas source (e.g., at a biogas plant at the landfill site or near the anaerobic digester) or at a centralized biogas plant (e.g., which receives raw, cleaned, or partially purified biogas from multiple sources). For example, a centralized biogas plant may be connected to one or more anaerobic digesters (e.g., each at a separate farm) via a biogas pipeline and/or grid. Alternatively, or additionally, the centralized biogas plant may receive biogas from one or more biogas sources by vehicle (e.g., see U.S. Pat. No. 10,760,024). In one embodiment, the biogas source is a centralized anaerobic digester, wherein the feedstock for anaerobic digestion is transported from multiple locations (e.g., multiple farms).

The upgraded biogas is transported to hydrogen production (e.g., to a stand-alone hydrogen plant or to a production facility having at least one hydrogen plant). As the upgraded biogas may be relatively pure (e.g., have a $CH_4$ content greater than about 92%), it may be transported using methods used to transport natural gas. For example, if the biogas is upgraded to RNG it can be transported in a CNG tanker (e.g., at a pressure of about 3600 psig) and/or transported by pipeline (e.g., a natural gas distribution system such as the US natural gas grid). In some cases, upgraded biogas that does not meet pipeline standards can be mixed with another gas (e.g., propane or fossil based natural gas) in order to facilitate injection into the natural gas distribution system.

In general, when upgraded biogas is transported by pipeline, it is transferred as a fluid (e.g., in gaseous or liquid form), and may be provided as a segregated batch or a fungible batch. The term "batch", as used herein, refers to a certain amount of the gas (e.g., energy delivered) and does not imply or exclude an interruption in the production and/or delivery.

When upgraded biogas is transported as a fungible batch in a natural gas distribution system, a quantity of the upgraded biogas (e.g., in MJ) is injected into the natural gas distribution system (optionally after being blended with another gas having a relatively high calorific value), where it can comingle with non-renewable natural gas, and an equivalent quantity of gas (e.g., in MJ) is withdrawn at another location (i.e., as long as there is a physical link between the injection point and the withdrawal point). Since the transfer or allocation of the environmental attributes of the upgraded biogas injected into the natural gas distribution system to gas withdrawn at a different location is typically recognized, the withdrawn gas is recognized as the upgraded biogas and/or qualifies as RNG under applicable regulations (e.g., even though the withdrawn gas may not contain actual molecules from the original biomass and/or contains methane from fossil sources). Such transfer may be carried out on a displacement basis, where transactions within the natural gas distribution system involve a matching and balancing of inputs and outputs. Typically, the direction of the physical flow of gas is not considered. Establishing that a gas is recognized as and/or qualifies as RNG (e.g., originates from renewable sources) under applicable regulations can depend on whether the gas is transported by truck or by pipeline and the practices and requirements of the applicable regulatory agency, where such practices may include, for example, the use of chain of custody accounting methods such as identity preservation, book-and-claim, and/or mass balance.

Transporting the upgraded biogas via a natural gas grid is particularly advantageous as it facilitates transporting the renewable feedstock anywhere where the grid delivers without significant additional cost (e.g., financially and/or GHG emissions). In one embodiment, the upgraded biogas is transported to hydrogen production, at least in part, via a natural gas distribution system. In one embodiment, the upgraded production is transported to hydrogen production, at least in part, by vehicle.

Hydrogen Production

In general, the renewable hydrogen may be produced at one or more hydrogen plants. The term "hydrogen plant", as used herein, refers to a system or combination of systems primarily used for hydrogen production. The term "renewable hydrogen", as used herein, refers to hydrogen produced using biogas (e.g., upgraded biogas and/or RNG). For example, the term "renewable hydrogen" can refer to hydrogen produced by methane reforming a feed withdrawn from a natural gas distribution system, when at least a portion of the withdrawn feed is recognized as and/or qualifies as RNG under applicable regulations.

In general, the hydrogen production may use any suitable technology known in the art that can convert upgraded biogas and/or natural gas to hydrogen. Examples of technologies that may be suitable include, but are not limited to, steam methane reforming (SMR), autothermal reforming (ATR), partial oxidation (PDX), and dry methane reforming (DMR). SMR, ATR, and DMR, which are types of catalytic reforming, may operate by exposing natural gas to a catalyst at high temperature and pressure to produce syngas. PDX reactions, which include thermal partial oxidation reactions (TPDX) and catalytic partial oxidation reactions (CPDX), may occur when a sub-stoichiometric fuel-oxygen mixture is partially combusted in a reformer. PDX also may be referred to as oxidative reforming. For purposes herein, the term "methane reforming" may refer to SMR, ATR, DMR, or PDX.

Of the various types of methane reforming, SMR is the most common. In SMR, which is an endothermic process, methane is reacted with steam under pressure in the presence of a catalyst to produce carbon monoxide (CO) and $H_2$ according to the following reaction:

$$CH_4 + H_2O + heat \rightarrow CO + 3H_2 \quad (1)$$

Referring to the hydrogen plant in FIG. 1, this reaction may occur in the SMR reactor tubes, which contain the reforming catalyst. Without being limiting, the catalyst may be nickel-based, the operating pressure may be between 200 psig (1.38 MPa) and 600 psig (4.14 MPa), and the operating temperature may be between about 450 to 1000° C. The heat required for the catalytic reforming of Eq. 1 can be provided by the combustion in the SMR burners (e.g., the combustion chamber may surround the reformer tubes in which the reaction is conducted).

The syngas produced from Eq. (1) may be further reacted in the WGS 20. The WGS is based on the water gas shift reaction, wherein carbon monoxide is converted to carbon dioxide and hydrogen:

$$CO + H_2O \rightarrow CO_2 + H_2 + \text{small amount of heat} \quad (2)$$

Providing WGS downstream of SMR increases the yield of $H_2$, and thus is commonly included in hydrogen production. For example, in addition to $H_2$, the syngas produced from the SMR may have a $CO_2$ content between about 7-10%, a CO content between about 12-19%, and a $CH_4$ content between about 2-6%, whereas the syngas produced from the WGS may have a $CO_2$ content between about 15-16%, a CO content between about 4-5%, and a $CH_4$ content between about 3-4%.

The gas produced from methane reforming (e.g., the syngas 25) is subjected to a hydrogen purification, wherein $H_2$ is separated from CO, $CO_2$, and/or $CH_4$ in one or more stages to produce a hydrogen product (e.g., containing at least 80% hydrogen). For example, in one embodiment, the hydrogen purification produces an enriched hydrogen stream having a hydrogen content of at least 90, 92, 94, 96, 98, 99, or 99.5%. In one embodiment, the hydrogen purification produces an enriched hydrogen stream having a hydrogen content of at least 99.9%. Without being limiting, some examples of suitable hydrogen purification technologies include, but are not limited to: a) absorption, b) adsorption, c) membrane separation, d) cryogenic separation, and e) methanation. Some examples of absorption systems that may be suitable include, but are not limited to, a monoethanolamine (MEA) unit or a methyl-diethanolamine (MDEA) unit. A MEA unit may include one or more absorption columns containing an aqueous solution of MEA at about 30 wt%. The outlet liquid stream of solvent may be treated to regenerate the MEA and separate $CO_2$. Some examples of adsorption systems that may be suitable include, but are not limited to, systems that use adsorbent bed (e.g., molecular sieves, activated carbon, active alumina, or silica gel) to remove impurities such as $CH_4$, $CO_2$, CO, $N_2$, and/or water from the syngas gas. For example, hydrogen purification systems that are based on PSA are commonly used for hydrogen plants, as such systems produces a purge gas that can be recycled to fuel the SMR burners, thereby improving energy efficiency (e.g., see FIG. 1). In one embodiment, hydrogen purification uses vacuum PSA system (VPSA). Some examples of membranes systems that may be suitable include, but are not limited to, $H_2$ selective membranes. A hydrogen purification unit that is based on cryogenic separation may cool the syngas gas down to temperatures where the impurities condense or sublimate and can be separated as a liquid or a solid fraction, while the hydrogen accumulates in the gas phase. For example, cryogenic separations may use temperatures below −10° C. or below −50° C. Methanation is a catalytic process that can be conducted to convert the residual carbon monoxide and/or carbon dioxide in the syngas to methane. For example, see equation 3.

$$CO+3H \rightarrow CH_4+H_2O \qquad (3)$$

Since the methanation reaction consumes hydrogen, a hydrogen purification unit that includes a methanation may include $CO_2$ removal prior to methanation.

In general, hydrogen production is well known and those skilled in the art will understand that the hydrogen plant(s) may use any suitable technology and/or have any suitable configuration. For example, the hydrogen production may be based on any suitable methane reforming technology combined with any suitable hydrogen purification. With specific regard to FIG. 1, those skilled in the art will understand that each of the SMR unit 10 and WGS unit 20 may include a single reactor or multiple reactors (e.g., the WGS unit 20 may include a high temperature WGS reactor (e.g., 350° C.) followed by a low temperature WGS reactor (e.g., 200° C.)), that the SMR reactor(s) may be top-fired reformers, side-fired reformers, bottom-fired reformers, etc., that the SMR reformer may be downstream of a purification unit to remove sulfur, chloride, olefin, and/or other compounds that may be detrimental to the SMR reforming catalysts, or that the SMR reformer may be downstream a pre-reforming unit, which allows a higher inlet feed temperature with minimal risk of carbon deposition. Those skilled in the art will also understand that although a steam methane reformer may be referred to as a "methane reformer," typically they can convert any of the hydrocarbons present in the natural gas to syngas (i.e., not just the methane).

In the above-described embodiments, the feedstock for the hydrogen production process contains the upgraded biogas (e.g., RNG), which can be transported to the hydrogen plant(s) by vehicle and/or as a fungible batch via a natural gas distribution system. In each embodiment, the feedstock may contain only the RNG or may contain both RNG and fossil based gas such as natural gas (e.g., the hydrogen can be produced by co-processing renewable and non-renewable methane). When the feed contains both RNG and fossil based gas, the quantity of renewable hydrogen produced can be determined using the renewable fraction of the feedstock (based on energy).

In the above-described embodiments, the feedstock for the renewable hydrogen process contains the upgraded biogas. However, in some embodiments, a portion of the upgraded biogas is fed to the combustion zone of the methane reformer (e.g., to the SMR burners). Since combusting upgraded biogas simply returns to the atmosphere carbon that was recently fixed by photosynthesis, and thus is considered relatively benign, this can reduce GHG emissions from the SMR furnace (e.g., compared to using fossil-based methane). Accordingly, the CI of renewable hydrogen produced by SMR of upgraded biogas produced from a landfill, wherein only the $CO_2$ from the feedstock is captured and stored, could be reduced to less than 11 $gCO_2e/MJ$. While it may be advantageous to sacrifice some of the upgraded biogas for fuel in order to improve the GHG balance of the hydrogen production and/or fuel production process, this reduces the yield of renewable hydrogen and/or the yield of renewable content of the fuel(s) produced. Accordingly, there may be a compromise between increasing the yield of renewable hydrogen/renewable content and decreasing the lifecycle GHG emissions, for a given quantity of upgraded biogas. As described herein, the CI can also be reduced to less than 11 $gCO_2e/MJ$ by capturing and storing biogenic $CO_2$ from the biogas (e.g., as part of biogas upgrading). In some cases, in order to reduce the GHG emissions of the fuel by feeding upgraded biogas to the SMR burners, the upgraded biogas (or at least the portion fed to the SMR burners) must be transported to hydrogen production as a segregated batch (e.g., this may be dependent on the regulatory agency).

In certain embodiments, low-carbon electricity such as renewable electricity is used to provide heat for the methane reforming (e.g., for SMR). Low-carbon electricity refers to electricity generated in a process that does not emit significant amounts of fossil-based carbon dioxide and/or is produced from renewable energy sources. Without being limiting, low-carbon electricity can include electricity produced using nuclear power, hydropower, solar power, wind power, geothermal power, wave power, tidal power, or electricity produced from the combustion of a low-carbon energy source (e.g., biomass, biogenic syngas, or hydrogen) or of a fossil-based energy source with CCS. In certain embodiments, heat required for the SMR is generated using renewable electricity (i.e., electricity produced using renewable energy sources such as hydropower, solar power, wind power, geothermal power, wave power, tidal power, etc.). In certain embodiments, the low-carbon electricity is generated from gasification of agricultural and/or solid waste.

In general, any suitable technology known in the art that can use electricity to produce a sufficient amount of heat for at least part of the methane reforming can be used. The low-carbon electricity can produce the heat for methane reforming directly (e.g., to power resistive or inductive heaters that provide the heat directly for the methane reforming) and/or indirectly (e.g., using a heat storage medium and/or heat transfer fluid). In certain embodiments, the methane reformer (e.g., SMR) is an electrically heated methane reformer (e.g., electrically heated SMR), wherein the heat that would have been generated with conventional fired burners is replaced with electrically generated heat. Such methane reformers are generally configured such that there is no flue gas, and thus no carbon emissions associated with the flue gas (e.g., carbon emissions of hydrogen production may be reduced by 20-50% relative to the conventional fired SMR). In these embodiments, capturing carbon dioxide from the syngas can remove most of the carbon dioxide produced by methane reforming from one point location. Advantageously, these reduced carbon emissions are achieved without having to remove carbon dioxide from the flue gas (e.g., which can have low partial pressures of carbon dioxide and/or include nitrogen).

Carbon Capture and Storage

Capture of $CO_2$ from the biogas (e.g., generated during anaerobic digestion) and/or capture of $CO_2$ produced during hydrogen production can be conducted using any suitable technology or combination of technologies that can capture $CO_2$ for storage. As the $CO_2$ may be part of a gas mixture (e.g., biogas, syngas, flue gas, etc.), the $CO_2$ capture can include and/or depend upon the separation of $CO_2$ from one or more other gas components in a gas mixture. Technology that may be suitable for separating $CO_2$ from one or more other gas components in a gas mixture includes, but is not limited to, absorption, adsorption, membrane separation, and cryogenic separation.

The $CO_2$ from the biogas (e.g., generated during anaerobic digestion) can be captured upstream of biogas upgrading, as part of biogas upgrading, and/or from a tail gas produced from biogas upgrading. For example, since biogas upgrading can inherently include steps where $CO_2$ is separated from $CH_4$, such steps can be part of the $CO_2$ capture process, or can facilitate the $CO_2$ capture process, thereby reducing capital and operating costs. Biogas upgrading, which typically focuses on providing a relatively pure product stream (e.g., greater than 95% CH4), can produce a tail gas that contains $CO_2$ separated from the $CH_4$ in addition to other non-methane components separated from the $CH_4$. For example, biogas upgrading units based on absorption, adsorption, or membrane separation, can produce a $CO_2$ rich tail gas that is too impure for $CO_2$ storage and/or transport without further purification and/or upstream removal of one or more components. However, in some cases, biogas upgrading (e.g., based on cryogenic separation), can yield both relatively pure $CH_4$ (e.g., greater than about 95% $CH_4$) and relatively pure $CO_2$ (e.g., greater than about 95% $CO_2$). While cryogenic biogas upgrading may require upstream biogas cleaning, it advantageously can provide the $CO_2$ is a form that facilitates transport by vehicle and/or a $CO_2$ distribution system (e.g., can provide the $CO_2$ in liquid or solid form).

The $CO_2$ generated during hydrogen production can be captured upstream of hydrogen purification (but downstream of methane reforming), as part of hydrogen purification, from a tail gas produced from hydrogen purification, and/or from the flue gas (if applicable). When hydrogen production includes SMR, the captured $CO_2$ can be derived from the feedstock for SMR and/or the fuel for SMR. For example, the $CO_2$ generated during SMR based hydrogen production can be captured from the syngas, the tail gas (e.g., purge gas from PSA), and/or the flue gas (see FIG. 1). Since hydrogen purification can inherently include steps where $CO_2$ is separated from $H_2$, such steps can be part of the $CO_2$ capture process, or can facilitate the $CO_2$ capture process, thereby reducing capital and operating costs. Hydrogen purification processes based on absorption, adsorption, and/or membrane separation are typically focused on provide a relatively pure product stream (e.g., greater than 95% $H_2$), and often produce a tail gas that contains $CO_2$ separated from the $H_2$ in addition to, for example, CO and $CH_4$. As this tail gas can contain $CH_4$, which can be used to fuel the SMR or elsewhere at the facility, or may need to be flared, the configuration of the system may need to take this into account. In one embodiment, the $CO_2$ produced from hydrogen production is only captured from the flue gas. In one embodiment, the $CO_2$ produced from hydrogen production is only captured from the tail gas (e.g., purge gas). In one embodiment, the $CO_2$ produced from hydrogen production is only captured from the syngas (e.g., downstream of WGS). In one embodiment, the $CO_2$ produced from hydrogen production is captured from the syngas and the flue gas from SMR. Capturing the $CO_2$ produced the syngas is particularly advantageous as a result of the total pressure of the syngas and partial pressure of $CO_2$ in the syngas. Those skilled in the art can readily select suitable technology and/or configurations.

Figure 3:
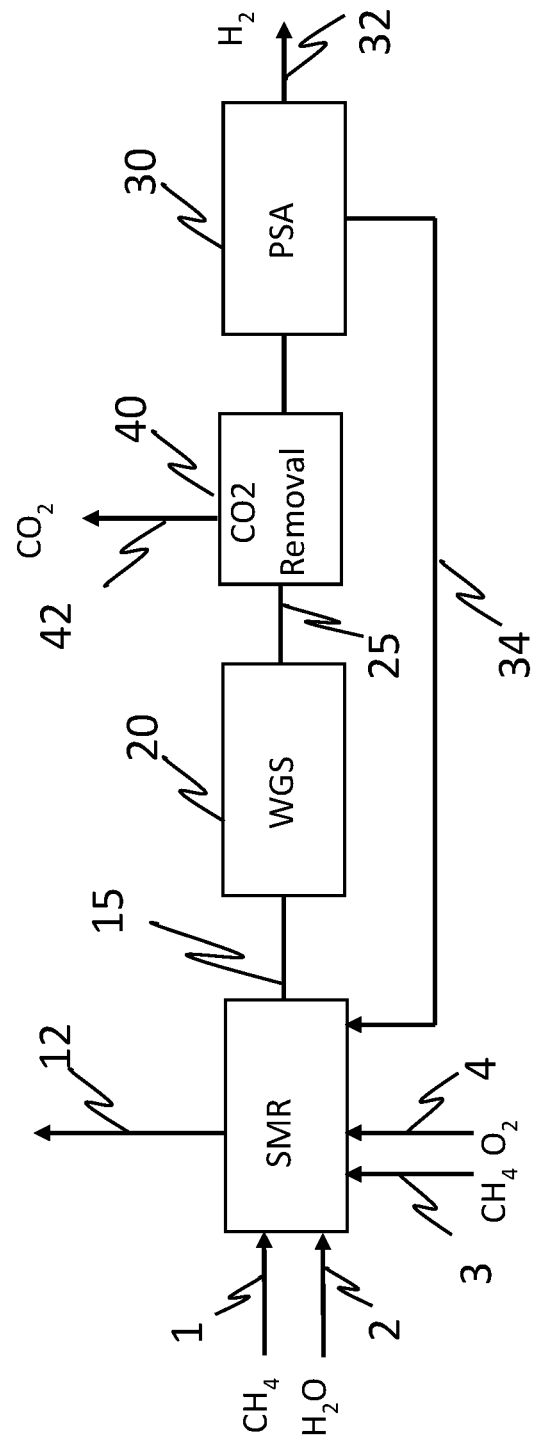
FIG. 3 is a simplified process flow diagram of another embodiment of an SMR based hydrogen plant.

In one embodiment, the process includes at least one separate $CO_2$ removal step for the $CO_2$ capture (i.e., separate from the biogas upgrading and/or hydrogen production). For example, in one embodiment, a separate $CO_2$ separation is conducted on the tail gas from biogas upgrading and/or on the tail gas from hydrogen purification to provide a $CO_2$ product that is sufficiently pure for $CO_2$ storage and/or transport. In another embodiment, a separate $CO_2$ separation is conducted upstream of biogas upgrading and/or hydrogen purification to provide a $CO_2$ product that is sufficiently pure for $CO_2$ storage and/or transport. For example, in the embodiment illustrated in FIG. 3, the syngas 25 is subjected to a $CO_2$ removal step 40 upstream of the PSA 30, which produces the $H_2$ product 32. The $CO_2$ removal step 40, which may for example be conducted using a MDEA capture unit, provides a $CO_2$ product 42 suitable geological storage and/or transport in a $CO_2$ distribution system (e.g., after dehydration and compression). The PSA 30 is then used to separate the $H_2$ from at least $CH_4$, thereby producing a $H_2$ product 32 and a purge gas 34 that is used to fuel the SMR burners.

In one embodiment, the biogas upgrading and/or hydrogen purification is conducted in stages and at least one stage of the biogas upgrading and/or hydrogen purification is a $CO_2$ capture step.

In one embodiment, the $CO_2$ capture step is integrated with the biogas upgrading and/or hydrogen production. For example, in one embodiment, the biogas upgrading and/or hydrogen production is selected to and/or modified to provide a $CO_2$ product suitable for geological storage and/or transport by a $CO_2$ distribution system (e.g., after dehydration and compression). In general, this may be achieved by selecting suitable separation technology and/or modifying the configuration of the system (e.g., removing one or more components upstream of the $CO_2$ separation). For example, in one embodiment, cryogenic $CO_2$ capture is part of biogas upgrading and/or hydrogen purification. When cryogenic separation is used as part of biogas upgrading, the biogas may be cleaned (e.g., to remove $H_2S$ and $H_2O$) and then subjected to a cryogenic separation that provides relatively pure $CO_2$ (e.g., >95% $CO_2$) while also providing a relatively pure $CH_4$ (e.g., >95% $CH_4$) and $N_2$ (if present). In one embodiment, vacuum pressure swing adsorption (VPSA) is used for biogas upgrading and/or hydrogen purification. For example, consider the hydrogen production in FIG. 1. If a VPSA unit, which includes a vacuum cycle, replaces the conventional PSA 30, then both $H_2$ purification and $CO_2$ capture can be integrated into a single separation unit. Integrating $H_2$ purification and $CO_2$ capture, and/or $CH_4$ purification and $CO_2$ capture, is particularly advantageous as the separation of $CO_2$ from other gases such as $N_2$, $CH_4$, or $H_2$, which may be present in gas mixtures such as biogas, syngas, flue gas, etc., can be one of the most energy intensive and/or expensive steps in CCS.

Storage of $CO_2$ captured from the biogas and/or storage of $CO_2$ captured from hydrogen production can be conducted using any suitable technology or combination of technologies. For example, carbon storage technologies, which are well known in the art, can sequester $CO_2$ in geological formations (i.e., subsurface formations). Suitable geological formations, which can occur in onshore or offshore settings, are often configured such that $CO_2$ injected therein, is trapped. Appropriate storage of the $CO_2$ can reduce GHG emissions and/or mitigate climate change. The level of GHG reduction achieved may be dependent on whether it is all biogenic, the applicable regulatory authority, the permanence of the storage, and/or whether its use displaces the use of fossil fuel products. In one embodiment, the captured $CO_2$ is sequestered in at least one geological formation. For example, in one embodiment the captured $CO_2$ is sequestered in a saline aquifer or is sequestered in an oil/natural gas reservoir as part of enhanced oil recovery (EOR). in one embodiment, the captured $CO_2$ is stored in concrete. In one embodiment, storage of the captured $CO_2$ permanently displaces fossil based. $CO_2$ emissions.

The purity of the $CO_2$ required for storage can be dependent upon the selected storage and/or selected mode of transportation, if applicable. For example, for geological sequestration and/or EOR, where the $CO_2$ is often transported, at least in part, via a $CO_2$ distribution system (e.g., pipeline), the $CO_2$ content should be as high as possible (e.g., at least about 95%). However, for some applications (e.g., bauxite residue carbonation, etc.) lower $CO_2$ contents may be suitable. In addition to a minimum $CO_2$ content, the $CO_2$ provided for storage and/or transport may have limits on the maximum amount of $H_2O$, $H_2S$, CO, $CH_4$, $N_2$, Ar, $H_2$, etc.

In general, when the $CO_2$ is captured far from storage, the process includes transporting the captured $CO_2$ to storage (e.g., by vehicle and/or a $CO_2$ distribution system). In order to transport $CO_2$ for storage, the $CO_2$ typically requires significant compression and/or cooling. When $CO_2$ is transported by vehicle (e.g., truck, ship, rail car) it is often transported as a liquid (e.g., a pressure of about 290 psig and a temperature of about −20° C., or a pressure of about 100 psig and a temperature of about −50° C.). When $CO_2$ is transported by a $CO_2$ distribution system (e.g., a $CO_2$ pipeline) it is often transported as a supercritical fluid (critical point is ~31° C., ~1070 psig). For example, many $CO_2$ pipelines are operated between about 1250 psig and about 2200 psig, or higher. In some embodiments, the collected $CO_2$ is also stored locally at a relatively high pressure (e.g., ~1600 psig) prior to transport by pipeline. In general, the $CO_2$ can be compressed to the desired pressure using a gas compressor, or alternatively, the collected $CO_2$ can be liquified at a lower pressure using a refrigeration system (e.g., 235 psig) and then pumped to the desired pressure. In one embodiment, the process produces a compressed stream of relatively pure $CO_2$ (e.g., at least 95% $CO_2$). In one embodiment, the $CO^2$ is transported to storage. at least in part, as a fungible batch using a $CO_2$ distribution system.

The $CO_2$ captured from the biogas upgrading and from the hydrogen production can be stored together or separately (e.g., in the same geological formation or in different geological formations). In general, how and where the captured $CO_2$ is stored may be dependent upon the closest storage site. In one embodiment, the $CO_2$ captured from the biogas upgrading and from the hydrogen production is, at least in part, transported using a $CO_2$ distribution system. In this embodiment, depending upon the distance between the biogas upgrading and the hydrogen production, the $CO_2$ captured from the biogas upgrading and from the hydrogen production may be injected at the same or different injection points of the $CO_2$ distribution system. For example, consider the embodiment in FIG. 4.

Figure 4:
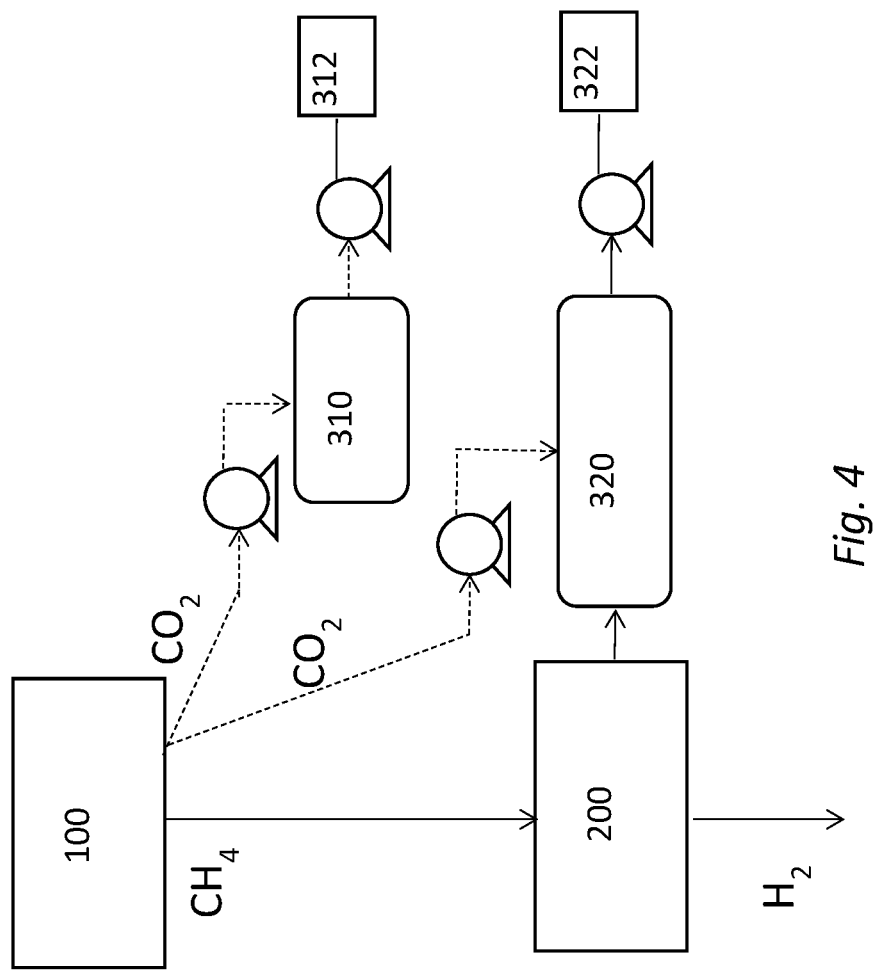
FIG. 4 is a schematic diagram illustrating how the $CO_2$ captured from the biogas upgrading and hydrogen production can be stored by injection into the same injection point of a $CO_2$ distribution system or using different injection points of the same or different $CO_2$ distribution systems.

In FIG. 4, the $CO_2$ captured from hydrogen production 200, which is optionally temporarily stored 320, is compressed (e.g., to 1800 psig) and injected into a first $CO_2$ distribution system at first injection point 322. The $CO_2$ captured from biogas upgrading 100 is compressed and liquified and transported by vehicle (e.g., rail car and/or tanker truck) for injection into the first injection point 322 or a second other injection point 312. The first and second injection points may be on the same $CO_2$ distribution system or different $CO_2$ distribution systems. Once transported, the $CO_2$ from biogas upgrading is unloaded from the vehicle (e.g., using a liquid $CO_2$ pump) into optional temporary storage 310, 320 before compression and injection. Transporting the $CO_2$ (e.g., 150, 250) by vehicle to an injection point of a $CO_2$ distribution system facilitates pooled injection. One skilled in the art would readily select the appropriate configuration in dependent upon distance between the biogas upgrading 100 and hydrogen production 200 and the proximity to a $CO_2$ distribution system.

In one embodiment, at least 50% of the $CO_2$ from the biogas is captured and stored. In one embodiment, at least 55%, at least 60%, at least 65%, at least 70%, at least 75%, at least 80%, at least 85%, at least 90% of the $CO_2$ from the biogas is captured and stored. In one embodiment, at least 55%, at least 60%, at least 65%, at least 70%, at least 75%, at least 80%, at least 85%, at least 90% of the $CO_2$ from the syngas is captured and stored. In one embodiment, at least 55%, at least 60%, at least 65%, at least 70%, at least 75%, at least 80%, at least 85%, at least 90% of the $CO_2$ produced from hydrogen production is captured and stored. In one embodiment, at least 55%, at least 60%, at least 65%, at least 70%, at least 75%, at least 80%, at least 85%, at least 90% of the each of the $CO_2$ from the biogas and the $CO_2$ from the syngas is captured and stored.

In one embodiment, the $CO_2$ captured and stored during hydrogen production includes at least 50%, at least 55%, at least 60%, at least 65%, at least 70%, at least 75%, at least 80%, at least 85%, at least 90% of the carbon in the transported upgraded biogas provided as feedstock for the methane reforming (on a mass of carbon basis). According to Eqs. (1) and (2), hydrogen production produces 1 mole of $CO_2$ from 1 mole of $CH_4$. If at least 50% of the carbon in the feedstock is captured and stored, then for about every 16 grams of methane provided as feedstock (i.e., 1 mole, containing 12 grams of carbon) at least about 22 grams of $CO_2$ is captured and stored (i.e., at least 0.5 moles, containing 6 grams of carbon, or 50% of the feedstock carbon input).

One advantage of the process(es)/system(s) of the instant disclosure it that low CI hydrogen can be produced without capturing and storing more than 70% of the $CO_2$ produced during hydrogen production (e.g., only capturing $CO_2$ derived from the feedstock) and/or when capturing less than 90% of the $CO_2$ from the biogas. Rather, negative CI hydrogen can be produced by capturing less than about 60%-65% from hydrogen production and capturing at least 50% of the $CO_2$ from the biogas upgrading, thereby providing a more economically feasible solution. Capturing a lower percentage of the $CO_2$ (e.g., <80%) from at least one of the stages is advantageous as it can be more energy intensive to remove the last 5-10% of a component.

Additionally, or alternatively, hydrogen can be produced without capturing and storing more than 70% of the $CO_2$ produced during hydrogen production (e.g., only capturing $CO_2$ derived from the feedstock) and/or when capturing less than 90% of the $CO_2$ from the biogas, by providing CCS of carbon obtained or derived from the biomass that is not present as $CO_2$. For example, in certain embodiments, carbon containing material obtained or derived from the digestate from anaerobic digestion of the biomass is provided for storage as part of CCS. In certain embodiments, the digestate is treated prior to CCS. For example, digestate can be subjected to a hydrothermal liquefaction to provide a bio-oil that can be sequestered. In some cases, the sequestration method is selected to prevent biodegradation of the material and/or trap GHGs in the event of biodegradation. In some cases, the material is treated in a process to reduce the potential for biodegradation. The amount of carbon obtained or derived from the digestate and provided as part of CCS can be expressed as kg C per $m^3$ (dry weight). Advantageously, storing a liquid or solid by-product produced from the process as part of CCS can further reduce the carbon intensity of the hydrogen produced and/or a fuel or product produced from the hydrogen. Further advantageously, this three-tiered CCS (e.g., where carbon is captured from the biogas and the digestate and from hydrogen production), can significantly reduce the lifecycle GHG emissions of the renewable hydrogen.

Fuel or Chemical Production

In general, the process produces renewable hydrogen and/or at least one fuel or chemical product produced using the renewable hydrogen. In one embodiment, the fuel is renewable hydrogen. For example, in one embodiment, the process produces renewable hydrogen that is used to power fuel cell electric vehicles (FCEVs), produce electricity (e.g., at a power plant), or used as rocket fuel. In one embodiment, the process produces fuel or chemical product using the renewable hydrogen. For example, in one embodiment, the process produces methanol using the renewable hydrogen. In one embodiment, the process produces fuel using the renewable hydrogen. For example, in one embodiment, the fuel is gasoline, diesel, and/or jet fuel. In one embodiment, the fuel is an aviation fuel. In one embodiment, the fuel is a transportation fuel. While producing renewable hydrogen for use as a fuel is advantageous, it is particularly advantageous when the renewable hydrogen is used to produce a transportation fuel. For example, using the renewable hydrogen to produce fuel can impart renewable content to the fuel and/or can reduce the CI of the fuel, particularly when the renewable hydrogen has a negative CI.

In general, the fuel may be produced by processing the renewable hydrogen with one or more other renewable feedstocks or one or more non-renewable feedstocks. When the process produces a fuel from the co-processing of renewable and non-renewable feedstocks, the fuel can have renewable content. The term "renewable content", as used herein, refers the portion of the fuel(s) that is recognized and/or qualifies as renewable (e.g., a biofuel) under applicable regulations. The quantification of the renewable content can be determined using any suitable method and is typically dependent upon the applicable regulations.

In one embodiment, the renewable hydrogen is used in the hydroprocessing (e.g., hydrocracking and/or hydrotreating) of crude-oil derived liquid hydrocarbon such that the renewable hydrogen is incorporated into a crude-oil derived liquid hydrocarbon to produce gasoline, diesel, and/or jet fuel having renewable content (e.g., see U.S. Pat. Nos. 8,658, 026, 8,753,854, 8,945,373, 9,040,271, 10,093,540, 10,421, 663, and 10,723,621, 10,981,784). In this embodiment, use of the renewable hydrogen can produce gasoline, diesel, and/or jet fuel having renewal content. Advantageously, such fuels can replace and/or be used with non-renewable gasoline, diesel, and/or jet fuel without affecting performance and/or operation (e.g., are drop-in fuels). Further advantageously, such fuels can be produced at existing oil refineries using existing equipment. The term "crude oil derived liquid hydrocarbon", as used herein, refers to any carbon-containing material obtained and/or derived from crude oil that is liquid at standard ambient temperature and pressure. The term "crude oil", as used herein, refers to petroleum extracted from geological formations (e.g., in its unrefined form). Crude oil includes liquid, gaseous, and/or solid carbon-containing material from geological formations, including oil reservoirs, such as hydrocarbons found within rock formations, oil sands, or oil shale. In one embodiment, the renewable hydrogen is used in the hydroprocessing (e.g., hydrocracking and/or hydrotreating) of crude-oil derived liquid hydrocarbon to produce aviation fuel having renewable content. This embodiment is particularly advantageous as it could help decarbonize commercial air travel and/or extend the life of older aircraft types by lowering their carbon footprint.

In one embodiment, the renewable hydrogen is used in the hydroprocessing (e.g., hydrocracking and/or hydrotreating) of renewable fats and/or oils (e.g., algae, jatropha, tallows, camelina, pyrolysis oil produced from biomass, etc.) to produce gasoline, diesel, and/or jet fuel. This embodiment is particularly advantageous as the resulting fuel can be fully renewable.

In general, the renewable hydrogen can be used in any suitable fuel or chemical production process. For example, in one embodiment, the renewable hydrogen is used in a Fischer-Tropsch type process to produce a liquid transportation fuel. In one embodiment, the renewable hydrogen is used as an industrial feedstock to produce one or more fuels and/or chemical products. In one embodiment, the renewable hydrogen is used to produce ammonia (e.g., in a Haber-Bosch process). In the Haber-Bosch process, which is well-known to those skilled in the art, nitrogen is converted to ammonia in a process conducted under high temperatures and pressures with a metal catalyst. Ammonia has an important role in the agricultural industry for production of fertilizers. Ammonia may also be used as a fuel and/or an energy carrier for energy storage and transportation.

In general, the renewable hydrogen may be produced at a commercial hydrogen plant or at a hydrogen plant at the fuel production facility. In both cases, the renewable hydrogen may be provided for fuel production via a $H_2$ pipeline or local $H_2$ pipe system as a fungible batch. More specifically, the renewable hydrogen may be allocated for the desired use (e.g., a specific fuel production process or a specific hydroprocessing unit). The term "allocating", as used herein in respect of a particular element, refers to designating the element for a specific purpose.

Carbon Intensity and/or Fuel Credits

In general, the carbon intensity of the fuel (e.g., renewable hydrogen or fuel produced using the renewable hydrogen) can be negative and/or relatively low because the $CO_2$ from both the biogas and the hydrogen production is captured and stored. While providing a zero carbon hydrogen is generally advantageous, it may be particularly advantageous if the CI is as low as possible when the hydrogen is used as a fuel or to produce a fuel, for fuel credit purposes.

Fuel credits are used to incentivize renewable fuels, often in the transportation sector. For example, fuel credits can be used to demonstrate compliance with some government initiative, standard, and/or program, where the goal is to reduce GHG emissions (e.g., reduce CI in transportation fuels as compared to some baseline level related to conventional petroleum fuels) and/or produce a certain amount of biofuel (e.g., produce a mandated volume or a certain percentage of biofuels). The target GHG reductions and/or target biofuel amounts may be set per year or for a given target date. Some non-limiting examples of such initiatives, standards, and/or programs include the Renewable Fuel Standard Program (RFS2) in the United States, the Renewable Energy Directive (RED II) in Europe, the Fuel Quality Directive in Europe, the Renewable Transport Fuel Obligation (RTFO) in the United Kingdom, and/or the Low Carbon Fuel Standards (LCFS) in California, Oregon, or British Columbia).

The term "fuel credit", as used herein, refers to any rights, credits, revenues, offsets, GHG gas rights, or similar rights related to carbon credits, rights to any GHG gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. A fuel credit can be a certificate, record, serial number or guarantee, in any form, including electronic, which evidences production of a quantity of fuel meeting certain life cycle GHG emission reductions relative to a baseline (e.g., a gasoline baseline) set by a government authority. Non-limiting examples of fuel credits include RINs and LCFS credits. A Renewable Identification Number (or RIN), which is a certificate that acts as a tradable currency for managing compliance under the RFS2, may be generated for each gallon of biofuel (e.g., ethanol, biodiesel, etc.) produced. A Low Carbon Fuel Standard (LCFS) credit, which is a certificate which acts as a tradable currency for managing compliance under California's LCFS, may be generated for each metric ton (MT) of $CO_2$ reduced.

In general, the requirements for generating or causing the generation of fuel credits can vary by country, the agency, and or the prevailing regulations in/under which the fuel credit is generated. In many cases, fuel credit generation may be dependent upon a compliance pathway (e.g., predetermined or applied for) and/or the biofuel meeting a predetermined GHG emission threshold. For example, with regard to the former, the RFS2 categorizes biofuel as cellulosic biofuel, advanced biofuel, renewable biofuel, and biomass-based diesel. With regard to the latter, to be a renewable biofuel under the RFS2, corn ethanol should have lifecycle GHG emissions at least 20% lower than an energy-equivalent quantity of gasoline (e.g., 20% lower than the 2005 EPA average gasoline baseline of 93.08 $gCO_2e/MJ$). In low carbon-related fuel standards, biofuels may be credited according to the carbon reductions of their pathway. For example, under California's LCFS, each biofuel is given a CI score indicating their GHG emissions as grams of $CO_2$ equivalent per megajoule (MJ) of fuel, and fuel credits are generated based on a comparison of their emissions reductions to a target or standard that may decrease each year (e.g., in 2019, ethanol was compared to the gasoline average CI of 93.23 $gCO_2e/MJ$), where lower CIs generate proportionally more credits. In one embodiment, the fuel produced is a transportation fuel, and a fuel credit is generated or is caused to be generated. In one embodiment, the transportation fuel and/or renewable content has lifecycle GHG emissions that are at least 20% less than the lifecycle GHG emissions of a gasoline baseline using EPA methodology, preferably at least 50% or 60% less.

With respect to renewable hydrogen produced according to the instant disclosure, it can be advantageous for the CI of the hydrogen to be as low as possible, particularly when the hydrogen is used as a fuel or to produce a fuel, so that more valuable fuel credits can be generated. In one embodiment, the process produces fuel (i.e., renewable hydrogen or fuel produced using the renewable hydrogen), where the renewable hydrogen has a CI that is not more than −10 $gCO_2e/MJ$, −20 $gCO_2e/MJ$, −30 $gCO_2e/MJ$, −40 $gCO_2e/MJ$, −50 $gCO2e/MJ$, −60 $gCO_2e/MJ$, or −70 $gCO_2/MJ$ of $H_2$. When the process produces a fuel from the co-processing of renewable and non-renewable feedstocks, the CI is measured for the resulting product from each of the co-processed feedstocks (i.e., there is a different CI for each the renewable and non-renewable feedstocks). In one embodiment, the process includes producing hydrogen associated with one or more producer credits.

EXAMPLE

Referring to Table 1, there is shown a list of estimated GHG emission values for hydrogen produced by various processes. As summarized in Table 2, these processes produce: 1) grey hydrogen from the SMR of natural gas with no CCS; 2) blue hydrogen from the SMR of natural gas with CCS (i.e., where the $CO_2$ is captured from the feedstock); 3) renewable hydrogen labelled "RH" from the SMR of RNG with no CCS; 4) renewable hydrogen labelled "RH+$CCS_{H2}$" from the SMR of RNG with CCS (i.e., where the $CO_2$ is captured from the feedstock only); 5) renewable hydrogen labelled "RH+$CCS_{H2}$+$CCS_{BG}$" from the SMR of RNG with CCS (i.e., where the $CO_2$ is captured from the feedstock and from the biogas); and 6) renewable hydrogen labelled "RH+$CCS_{BG}$" from the SMR of RNG with CCS (i.e., where the $CO_2$ is captured from the biogas only).

For each process, it was assumed that the fuel for the SMR burners is fossil based natural gas and that the feedstock for the methane reforming is RNG produced from landfill gas (i.e., is upgraded landfill gas). In order to compare the different processes, which can use different feedstocks, the GHG emissions for the hydrogen production were split into the contributions from the feedstock (i.e., upstream emissions) and from the hydrogen production. Each emission (positive number) and emission credit (negative number) is an estimation based on one or more published values and/or determined using stoichiometry. For example, the feedstock emissions of 10 $gCO_2e/MJ$ of $H_2$ for natural gas and 35 $gCO_2e/MJ$ of $H_2$ for landfill gas are estimated from the CA-GREET 3.0 model. The feedstock emission credit of −42 $gCO_2e/MJ$ of $H_2$, which is a net credit at least partially based on theoretical calculations, assumes that the emissions for CCS of the biogas is 5 $gCO_2e/MJ$ of $H_2$. For the hydrogen production, emissions from the combustion of fuel for the SMR burners is assumed to be 28 $gCO_2e/MJ$ of $H_2$, electricity is assumed to be 2 $gCO_2e/MJ$ of $H_2$, and emissions from the conversion of the feedstock to syngas is assumed to be 60 $gCO_2e$ per MJ of $H_2$. Assuming all of the $CO_2$ from the feedstock is captured and stored, and if the CCS process from hydrogen production results in 5 $gCO_2e/MJ$ of $H_2$ of emissions, the $CCS_{H2}$ process provides a net credit of −55 $gCO_2e/MJ$ of $H_2$.

TABLE 1

GHG Emission Values, in $gCO_2e/MJ$ of $H_2$, for various SMR based $H_2$ production processes

| Process | Feedstock | Feedstock $CO_2$ capture | Fuel Combustion | Feedstock conversion | Electricity | Plant $CO_2$ capture | CI |
|---|---|---|---|---|---|---|---|
| Grey $H_2$ | 10 | | 28 | 60 | 2 | | 100 |
| Blue $H_2$ | 10 | | 28 | 60 | 2 | −55 | 45 |
| RH | 35 | | 28 | | 2 | | 65 |
| RH + $CCS_{H2}$ | 35 | | 28 | | 2 | −55 | 11 |
| RH + $CCS_{H2}$ + $CCS_{BG}$ | 35 | −42 | 28 | | 2 | −55 | −31 |
| RH + $CCS_{BG}$ | 35 | −42 | 28 | | 2 | | 24 |

TABLE 2

Summary of the various SMR based $H_2$ production processes

| Process | Description | Feedstock | $CO_2$ capture |
|---|---|---|---|
| 1 | Grey $H_2$ | Natural Gas | None |
| 2 | Blue $H_2$ | Natural Gas | Yes - Syngas |
| 3 | Renewable $H_2$ (RH) | RNG (landfill) | None |
| 4 | Renewable $H_2$ and $CCS_{H2}$ | RNG (landfill) | Yes - Syngas only |
| 5 | Renewable $H_2$ and $CCS_{H2}$ and $CCS_{BG}$ | RNG (landfill) | Yes - Syngas and upstream |
| 6 | Renewable $H_2$ and $CCS_{BG}$ | RNG (landfill) | Yes - upstream only |

While the GHG emission values in Table 1 are estimations provided for comparative purposes, they do appear reasonable. For example, Table 1 lists the CI of grey hydrogen as 100 $gCO_2e/MJ$, which is within a published range of 94.8 to 101.4 g $CO_2e/MJ$. With regard to the CI of blue hydrogen, which Table 1 lists as 45 $gCO_2e/MJ$ (with CCS of about 60% of the total $CO_2$ produced), some published values are 19.6 $gCO_2e/MJ$ (with CCS of about 90% of the total $CO_2$ produced) and 34.5 $gCO_2e/MJ$ (with CCS of about 80% of the total $CO_2$ produced).

As evident from Table 1, simply using RNG as a feedstock, using RNG as a feedstock and capturing $CO_2$ from the feedstock, or using RNG as a feedstock and capturing $CO_2$ from the biogas, does not necessarily produce hydrogen having a negative CI, and can produce hydrogen having a higher CI than green hydrogen (e.g., which can be less than 10 $gCO_2e/MJ$).

However, by including the capture and storage of both $CO_2$ from the biogas and $CO_2$ derived from the feedstock for hydrogen production, the CI of the resulting renewable hydrogen is not only negative, but is quite low at −31 $gCO_2e/MJ$. Advantageously, this low value is achieved without having to capture and store $CO_2$ from the flue gas, without having to sacrifice a portion of the RNG to fuel the SMR, and/or without having to use RNG having a negative CI.

Of course, the above embodiments have been provided as examples only. It will be appreciated by those of ordinary skill in the art that various modifications, alternate configurations, and/or equivalents will be employed without departing from the scope of the invention. For example, although the instant disclosure provides a process that provides renewable hydrogen having a negative CI without CCS of $CO_2$ from the flue gas, without sacrificing a portion of the RNG to fuel the SMR, and/or without using a negative CI RNG, in some embodiments, the CI of the renewable hydrogen is further reduced by capturing and storing $CO_2$ from the flue gas, using a portion of the RNG to fuel the SMR, and/or using RNG having a negative CI (e.g., based on the anaerobic digestion of manure). For example, in the above described example, while the carbon intensity of the hydrogen is dependent on capturing and storing $CO_2$ from the biogas and from the feedstock for hydrogen production, it is also dependent on the carbon intensity of the RNG and/or other factors. Using RNG having a negative value can further reduce the carbon intensity of the hydrogen. Accordingly, the scope of the invention is therefore intended to be limited solely by the scope of the appended claims,

The invention claimed is:

1. A method of producing low carbon intensity hydrogen, the method comprising:
   providing transported upgraded biogas for a hydrogen production process, the transported upgraded biogas produced from a biogas upgrading process comprising:
   a) subjecting biogas comprising methane and carbon dioxide to biogas upgrading, thereby producing the upgraded biogas,
   b) capturing a first quantity of carbon dioxide and providing the first quantity of carbon dioxide for storage, the first quantity of carbon dioxide captured (i) as part of the biogas upgrading, (ii) from a stream produced from the biogas upgrading, or (iii) a combination of (i) and (ii), and
   c) transporting the upgraded biogas;
   generating hydrogen from the hydrogen production process using fossil-based natural gas and the transported upgraded biogas, the hydrogen production process comprising methane reforming and hydrogen purification, the methane reforming producing syngas comprising carbon dioxide and hydrogen, the hydrogen purification comprising purifying at least one of the syngas or a stream derived from the syngas to produce the low carbon intensity hydrogen; and
   capturing a second quantity of carbon dioxide from the hydrogen production process, and providing the second quantity of carbon dioxide for storage,
   wherein the low carbon intensity hydrogen has a carbon intensity that is dependent, at least in part, on storage of the first and second quantities of carbon dioxide.

2. The method according to claim 1, wherein the second quantity of carbon dioxide comprises biogenic carbon dioxide generated from the transported upgraded biogas and fossil based carbon dioxide generated from the fossil-based natural gas.

3. The method according to claim 1, wherein at least some of the carbon dioxide in the second quantity is removed from at least one of (i') the syngas or (ii') a stream at least partially derived from the syngas.

4. The method according to claim 3, wherein the methane reforming comprises steam methane reforming, the steam methane reforming producing flue gas, and wherein at least some of the carbon dioxide in the second quantity is removed from the flue gas.

5. The method according to claim 1, wherein all of the carbon dioxide in the second quantity is removed from at least one of (i') the syngas or (ii') a stream at least partially derived from the syngas.

6. The method according to claim 1, wherein the methane reforming comprises steam methane reforming, the steam methane reforming producing flue gas, and wherein all of the carbon dioxide in the second quantity is removed from the flue gas.

7. The method according to claim 1, wherein storage of the first and second quantities of carbon dioxide comprises geological sequestration.

8. The method according to claim 1, wherein at least a portion of the transported upgraded biogas is used as feedstock for the methane reforming.

9. The method according to claim 8, wherein at least a portion of the fossil-based natural gas is used as feedstock for the methane reforming.

10. The method according to claim 8, wherein the methane reforming comprises steam methane reforming, and wherein at least a portion of the transported upgraded biogas is fed to a combustion zone of the steam methane reformer.

11. The method according to claim 1, wherein at least a portion of the fossil-based natural gas is used as feedstock for methane reforming.

12. The method according to claim 1, wherein the methane reforming comprises steam methane reforming, and wherein at least a portion of the transported upgraded biogas is fed to a combustion zone of the steam methane reformer.

13. The method according to claim 1, wherein transporting the upgraded biogas comprises transporting at least a portion of the upgraded biogas to the hydrogen plant as a fungible batch.

14. The method according to claim 1, wherein transporting the upgraded biogas comprises transporting at least a portion of the upgraded biogas to the hydrogen plant as a segregated batch.

15. The method according to claim 1, wherein the second quantity of carbon dioxide contains not more than 75% of a total amount of carbon dioxide produced from hydrogen production.

16. The method according to claim 1, wherein the biogas is landfill gas.

17. The method according to claim 16, wherein the biogas is produced from anaerobic digestion of organic waste, swine manure, dairy manure, or any combination thereof.

18. The method according to claim 1, further comprising providing the low carbon intensity hydrogen for use in ammonia production.

19. The method according to claim 1, further comprising providing the low carbon intensity hydrogen for use in producing a fuel.

20. The method according to claim 19, wherein the fuel is produced in a fuel production process comprising hydrogenating crude oil derived liquid hydrocarbon with the low carbon intensity hydrogen.

21. The method according to claim 1, wherein the low carbon intensity hydrogen has a carbon intensity that is less than 11 $gCO_2eq/MJ$.

22. A method of producing low carbon intensity hydrogen, the method comprising:
provided transported upgraded biogas for a hydrogen production process, the transported upgraded biogas produced from a process comprising:
   a) subjecting biogas comprising methane and carbon dioxide to biogas upgrading, thereby producing the upgraded biogas, and
   b) transporting the upgraded biogas; and
generating hydrogen from the hydrogen production process using fossil-based natural gas and the transported upgraded biogas, the hydrogen production process comprising methane reforming and hydrogen purification, the methane reforming producing syngas comprising carbon dioxide and hydrogen, the hydrogen purification comprising purifying at least one of the syngas or a stream derived from the syngas to produce the low carbon intensity hydrogen,
wherein a first quantity of carbon dioxide is captured and provided for storage, transport, or a combination thereof, the first quantity of carbon dioxide captured (i) as part of the biogas upgrading, (ii) from a stream produced from the biogas upgrading, or (iii) a combination of (i) and (ii),
wherein a second quantity of carbon dioxide is captured and provided for storage, transport, or a combination thereof, the second quantity of carbon dioxide captured from the hydrogen production process, and
wherein the low carbon intensity hydrogen has a carbon intensity that is less than 11 $gCO_2eq/MJ$.

23. The method of producing low carbon intensity hydrogen according to claim 22, wherein the low carbon intensity hydrogen has a carbon intensity that is less than 0 $gCO_2eq/MJ$.

* * * * *

UNITED STATES PATENT AND TRADEMARK OFFICE
CERTIFICATE OF CORRECTION

| | | |
|---|---|---|
| PATENT NO. | : 11,760,630 B2 | Page 1 of 2 |
| APPLICATION NO. | : 18/069041 | |
| DATED | : September 19, 2023 | |
| INVENTOR(S) | : Patrick J. Foody | |

It is certified that error appears in the above-identified patent and that said Letters Patent is hereby corrected as shown below:

On the Title Page

Item [57], Line 6, delete "gCO$_2$-eq" and insert -- gCO$_2$eq --.

Page 2, item [56], Line 20, delete "2003/0011141" and insert -- 2003/0111410 --.

In the Specification

Column 2, Line 61, delete "CO2" and insert -- CO$_2$ --.

Column 7, Line 44, delete "least $_{950}$ BTU/scf." and insert -- least 950 BTU/scf. --.

Column 10, Line 16, delete "CO2)." and insert -- CO$_2$). --.

Column 16, Line 22, delete "unit." and insert -- unit). --.

Column 19, Line 7, delete "CO+3H" and insert -- CO+3H$_2$ --.

Column 19, Line 7, delete "($^3$)" and insert -- (3) --.

Column 23, Line 35, delete "CO$^2$" and insert -- CO$_2$ --.

Column 23, Line 35, delete "storage." and insert -- storage, --.

Column 27, Line 11, delete "Columbia)." and insert -- Columbia." --.

Column 27, Line 39, delete "and or" and insert -- and/or --.

Column 28, Line 12, delete "gCO2e/MJ," and insert -- gCO$_2$e/MJ, --.

Signed and Sealed this
Twenty-fourth Day of September, 2024

Katherine Kelly Vidal
*Director of the United States Patent and Trademark Office*

In the Claims

Column 30, Line 66, Claim 2, delete "fossil based" and insert -- fossil-based --.